(12) United States Patent
Sherman et al.

(10) Patent No.: US 7,927,852 B2
(45) Date of Patent: *Apr. 19, 2011

(54) AGGREGATE-FREE URATE OXIDASE FOR PREPARATION OF NON-IMMUNOGENIC POLYMER CONJUGATES

(75) Inventors: Merry R. Sherman, San Carlos, CA (US); Mark G. P. Saifer, San Carlos, CA (US); L. David Williams, Fremont, CA (US); Michael S. Hershfield, Durham, NC (US); Susan J. Kelly, Chapel Hill, NC (US)

(73) Assignee: Mountain View Pharmaceuticals, Inc., Menlo Park, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 11/882,750

(22) Filed: Aug. 3, 2007

(65) Prior Publication Data

US 2008/0057048 A1    Mar. 6, 2008

Related U.S. Application Data

(60) Continuation of application No. 10/928,370, filed on Aug. 30, 2004, which is a continuation of application No. 09/501,730, filed on Feb. 10, 2000, now Pat. No. 6,783,965, and a continuation-in-part of application No. 09/839,946, filed on Apr. 19, 2001, now Pat. No. 7,723,089, which is a division of application No. 09/370,084, filed on Aug. 6, 1999, now Pat. No. 6,576,235.

(60) Provisional application No. 60/219,318, filed on Aug. 6, 1998.

(51) Int. Cl.
*C12N 9/04* (2006.01)
*C12N 15/00* (2006.01)
*A61K 38/44* (2006.01)
*C07K 1/00* (2006.01)

(52) U.S. Cl. ....... 435/190; 435/191; 435/440; 424/94.4; 530/350

(58) Field of Classification Search ........... None
See application file for complete search history.

(56) References Cited

U.S. PATENT DOCUMENTS

| 3,616,231 A | 10/1971 | Bergmeyer et al. |
| 4,179,337 A | 12/1979 | Davis et al. |
| 4,460,683 A | 7/1984 | Gloger et al. |
| 4,766,106 A | 8/1988 | Katre et al. |
| 4,847,079 A | 7/1989 | Kwan |
| 4,847,325 A | 7/1989 | Shadle et al. |
| 4,917,888 A | 4/1990 | Katre et al. |
| 5,122,614 A | 6/1992 | Zalipsky |
| 5,283,317 A | 2/1994 | Saifer et al. |
| 5,286,637 A | 2/1994 | Veronese et al. |
| 5,382,518 A | 1/1995 | Caput et al. |
| 5,428,128 A | 6/1995 | Mensi-Fattohi et al. |
| 5,458,135 A | 10/1995 | Patton et al. |
| 5,468,478 A | 11/1995 | Saifer et al. |
| 5,541,098 A | 7/1996 | Caput et al. |
| 5,612,460 A | 3/1997 | Zalipsky |
| 5,643,575 A | 7/1997 | Martinez et al. |
| 5,653,974 A | 8/1997 | Hung et al. |
| 5,711,944 A | 1/1998 | Gilbert et al. |
| 5,762,923 A | 6/1998 | Gross et al. |
| 5,811,096 A | 9/1998 | Aleman et al. |
| 5,824,784 A | 10/1998 | Kinstler et al. |
| 5,880,255 A | 3/1999 | Delgado et al. |
| 5,919,455 A | 7/1999 | Greenwald et al. |
| 5,932,462 A | 8/1999 | Harris et al. |
| 5,955,336 A | 9/1999 | Shigyo et al. |
| 6,201,110 B1 | 3/2001 | Olsen et al. |
| 6,576,235 B1 | 6/2003 | Williams et al. |
| 6,783,965 B1 | 8/2004 | Sherman et al. |
| 6,913,915 B2 | 7/2005 | Ensor et al. |
| 7,723,089 B2 | 5/2010 | Williams et al. |
| 2002/0010319 A1 | 1/2002 | Ansaldi et al. |
| 2003/0166249 A1 | 9/2003 | Williams et al. |
| 2005/0014240 A1 | 1/2005 | Sherman et al. |
| 2008/0031864 A1 | 2/2008 | Williams et al. |

FOREIGN PATENT DOCUMENTS

| DE | 279 486 A1 | 6/1990 |
| EP | 0 043 980 A2 | 1/1982 |
| JP | 55-99189 | 7/1980 |
| JP | 55-135590 A | 10/1980 |
| JP | 62-55079 | 3/1987 |
| JP | 03-148298 | 6/1991 |
| JP | 09-154581 | 6/1997 |
| WO | WO 94/19007 A1 | 9/1994 |
| WO | WO 98/31383 A1 | 7/1998 |
| WO | WO 00/07629 A2 | 2/2000 |

(Continued)

OTHER PUBLICATIONS

Patent Abstract of Japan, English language abstract of JP 55-135590 A (Document FP11), 1990.

Francis, G.E., et al., "PEGylation of cytokines and other therapeutic proteins and peptides: the importance of biological optimisation of coupling techniques," *Int. J. Hematology* 68:1-18, Elsevier Science Ireland Ltd. (1998).

Kral, L.G., et al., "Cloning a cDNA for *Drosophila melanogaster* urate oxidase," *Gene* 45:131-137, Elsevier Science Publishers B.V. (1986).

(Continued)

*Primary Examiner* — Robert Landsman
*Assistant Examiner* — Ian Dang
(74) *Attorney, Agent, or Firm* — Sterne, Kessler, Goldstein & Fox P.L.L.C.

(57) ABSTRACT

A naturally occurring or recombinant protein, especially a mutein of porcine urate oxidase (uricase), that is essentially free of large aggregates can be rendered substantially non-immunogenic by conjugation with a sufficiently small number of strands of polymer such that the bioactivity of the protein is essentially retained in the conjugate. Such conjugates are unusually well suited for treatment of chronic conditions because they are less likely to induce the formation of antibodies and/or accelerated clearance than are similar conjugates prepared from protein preparations containing traces of large aggregates.

40 Claims, 6 Drawing Sheets

FOREIGN PATENT DOCUMENTS

WO    WO 00/08196 A3    2/2000
WO    WO 01/59078 A2    8/2001

OTHER PUBLICATIONS

Wang, L.-W.C., and Marzluf, G.A., "Purification and Characterization of Uricase, a Nitrogen-Regulated Enzyme, from *Neurospora crassa,*" Ardis. Biochem. Biophys. 201:185-193, Academic Press, Inc. (1980).

Abuchowski, A., et al., "Effect of Covalent Attachment of Polyethylene Glycol on Immunogenicity and Circulating Life of Bovine Liver Catalase," J. Biol. Chem. 252:3582-3586, American Society for Biochemistry and Molecular Biology (1977).

Abuchowski, A., et al., "Reduction of Plasma Urate Levels in the Cockerel with Polyethylene Glycol-Uricase," J. Pharmacol. Exp. Ther. 219:352-354, The American Society for Pharmacology and Experimental Therapeutics (1981).

Alvares, K., et al., "The Nucleotide Sequence of a Full Length cDNA Clone Encoding Rat Liver Urate Oxidase," Biochem. Biophys. Res. Commun. 158:991-995, Academic Press, Inc. (1989).

Alvares, K., et al., "Rat urate oxidase produced by recombinant baculovirus expression: Formation of peroxisome crystallized core-like structures," Proc. Natl. Acad. Sci. USA 89:4908-4912, National Academy of Sciences (1992).

Braun, A. and Alsenz, J., "Development and Use of Enzyme-Linked Immunosorbent Assays (ELISA) for the Detection of Protein Aggregates in Interferon-Alpha (IFN-α) Formulations," Pharm. Res. 14:1394-1400, Plenum Publishing Corporation (Oct. 1997).

Braun, A., et al., "Protein Aggregates Seem to Play a Key Role Among the Parameters Influencing the Antigenicity of Interferon Alpha (IFM-α) in Normal and Transgenic Mice," Pharm. Res. 14:1472-1478, Plenum Publishing Corporation (Oct. 1997).

Burnham, N.L., "Polymers for delivering peptides and proteins," Am. J. Hosp. Pharm. 51:210-218, American Society of Hospital Pharmacists, Inc. (1994).

Caliceti, P., et al., "Biopharmaceutical Properties of Uricase Conjugated to Neutral and Amphiphilic Polymers," Bioconjugate Chem. 10:638-646, American Chemical Society (Jul.-Aug. 1999).

Chen, R.H.-L., et al., "Properties of Two Urate Oxidases Modified by the Covalent Attachment of Poly(Ethylene Glycol)," Biochim. Biophys. Acta 660:293-298, Elsevier/North Holland Biomedical Press (1981).

Chua, C.C., et al., "Use of Polyethylene Glycol-Modified Uricase (PEG-Uricase) to Treat Hyperuricemia in a Patient with Non-Hodgkin Lymphoma," Ann. Intern. Med. 109:114-117, American College of Physicians (1988).

Colloc'h, N., et al., "Crystal Structure of the protein drug urate oxidase-inhibitor complex at 2.05 Å resolution," Nature Struct. Biol. 4:947-952, Nature Publishing Company (Nov. 1997).

Conley, T.G. and Priest, D.G., "Thermodynamics and Stoicheiometry of the Binding of Substrate Analogues to Uricase," Biochem. J. 187:727-732, The Biochemical Society (1980).

Davis, F.F., et al., "Enzyme-Polyethylene Glycol Adducts: Modified Enzymes with Unique Properties," in: Enzyme Engineering, vol. 4, Braun, G.B., et al., eds., Plenum Press, New York, pp. 169-173 (1978).

Davis, S., et al., "Hypouricaemic Effect of Polyethyleneglycol Modified Urate Oxidase," Lancet 2:281-283, Lancet Publishing Group (1981).

Donadio, D., et al., "Manifestation de type anaphylactique après injection intra-veineuse d'urate-oxydase chez un enfant asthmatique atteint de leucémie aiguë," La Nouv. Presse Med. 10:711-712, Masson (1981).

Unverified English language partial translation of Donadio, D., et al., "Anaphylaxis-like manifestations after intravenous injection of urate oxidase in an asthmatic child with acute leukemia," La Nouv. Presse Med. 10:711-712, Masson (1981) (Document NPL15).

Fam, A.G., "Strategies and Controversies in the Treatment of Gout and Hyperuricaemia," Ballière's Clinical Rheumatology 4:177-192, Ballière Tindall (1990).

Fridovich, I., "The Competitive Inhibition of Uricase by Oxonate and by Related Derivatives of s-Triazines," J. Biol. Chem. 240:2491-2494, American Society for Biochemistry and Molecular Biology (1965).

Fuertges, F., and Abuchowski, A., "The Clinical Efficacy of Poly(Ethylene Glycol)-Modified Proteins," J. Control. Release 11:139-148, Elsevier Science (1990).

Fujita, T., et al., "Tissue Distribution of $^{111}$In-Labeled Uricase Conjugated with Charged Dextrans and Polyethylene Glycol," J. Pharmacobio-Dyn. 14:623-629, Pharmaceutical Society of Japan (1991).

Greenberg, M.L. and Hershfield, M.S., "A Radiochemical-High-Performance Liquid Chromatographic Assay for Urate Oxidase in Human Plasma," Anal. Biochem. 176:290-293, Academic Press, Inc. (1989).

Hande, K.R., et al., "Severe Allopurinol Toxicity. Description and Guidelines for Prevention in Patients with Renal Insufficiency," Am. J. Med. 76:47-56, Excerpta Medica (1984).

Hedlund, L.W., et al., "Magnetic Resonance Microscopy of Toxic Renal Injury Induced by Bromoethylamine in Rats," Fundam. Appl. Toxicol. 16:787-797, Academic Press (1991).

Henney, C.S. and Ellis, E.F., "Antibody Production to Aggregated Human γG-Globulin in Acquired Hypogammaglobulinemia," New Engl. J. Med. 278:1144-1146, Massachusetts Medical Society (1968).

Herbst, R., et al., "Folding of Firefly (*Photinus pyralis*) Luciferase: Aggregation and Reactivation of Unfolding Intermediates," Biochem. 37:6586-6597, American Chemical Society (May 1998).

Hershfield, M.S., et al., "Use of Site-Directed Mutagenesis to Enhance the Epitope-shielding Effect of Covalent Modification of Proteins with Polyethylene Glycol," Proc. Natl. Acad. Sci. USA 88:7185-7189, National Academy of Sciences (1991).

Hershfield, M.S., "Biochemistry and Immunology of Poly(ethylene glycol)-Modified Adenosine Deaminase (PEG-ADA)," in: ACS Symposium Series 680. Poly(ethylene glycol). Chemsitry and Biological Applications, Harris, J.M. and Zalipsky, S., eds., American Chemical Society, Washington, DC, pp. 145-154 (first available Apr. 1997).

Ishino, K. and Kudo, S., "Protein Concentration Dependence on Aggregation Behavior and Properties of Soybean 7S and 11S Globulins during Alkali-treatment," Agric. Biol. Chem. 44:1259-1266, Agricultural Chemical Society of Japan (1980).

Ito, M., et al., "Identification of an Amino Acid Residue Involved in the Substrate-binding Site of Rat Liver Uricase by Site-directed Mutagenesis," Biochem. Biophys. Res. Commun. 187:101-107, Academic Press (1992).

Kahn, K., and Tipton, P.A., "Kinetic Mechanism and Cofactor Content of Soybean Root Nodule Urate Oxidase," Biochemistry 36:4731-4738, American Chemical Society (Apr. 1997).

Kelly, S.J., et al., "Diabetes Insipidus in Uricase-Deficient Mice: A Model for Evaluating Therapy with Poly(Ethylene Glycol)-Modified Uricase," J. Am. Soc. Nephrol. 12:1001-1009, Lippincott Williams & Wilkins (May 2001).

Kito, M., et al., "A Simple and Efficient Method for Preparation of Monomethoxypolyethylene Glycol Activated with p-Nitrophenylchloroformate and Its Application to Modification of L-Asparaginase," J. Clin. Biochem. Nutr. 21:101-111, Institute of Applied Biochemistry (1996).

Kunitani, M., et al., "On-line characterization of polyethylene glycol-modified proteins," J. Chromat. 588:125-137, Elsevier Science Publishers B.V. (1991).

Kunitani, M., et al., "Classical light scattering quantitation of protein aggregates: off-line spectroscopy versus HPLC detection," J. Pharm. Biomed. Anal. 16:573-586, Elsevier Science B.V. (Dec. 1997).

Leach, M., et al., "Efficacy of Urate Oxidase (Uricozyme) in Tumour Lysis Induced Urate Nephropathy," Clin. Lab. Haematol. 20:169-172, Blackwell Scientific Publications (Jun. 1998).

Lee, C.C., et al., "Generation of cDNA Probes Directed by Amino Acid Sequence: Cloning of Urate Oxidase," Science 239:1288-1291, American Association for the Advancement of Science (1988).

Legoux, R., et al., "Cloning and Expression in *Escherichia coli* of the Gene Encoding *Aspergillus flavus* Urate Oxidase," J. Biol. Chem. 267:8565-8570, American Society for Biochemistry and Molecular Biology (1992).

Mahmoud, H.H., et al., "Advances in the Management of Malignancy-Associated Hyperuricaemia," *Br. J. Cancer (Supplement 4)* 77:18-20, Churchill Livingstone (Jun. 1998).

Mahler, H.R., et al., "Studies of Uricase. I. Preparation, Purification, and Properties of a Cuproprotein," *J. Biol. Chem.* 216:625-641, American Society for Biochemistry and Molecular Biology (1955).

Malakhova, E.A., et al., "Kinetic Properties of Bacterial Urate Oxidase Entrapped in Hydrated Reversed Micelles," *Biologicheskie Membrany* 8:453-459, Nauka (1991).

Miura, S., et al., "Urate Oxidase is Imported into Peroxisomes Recognizing the C-terminal SKL Motif of Proteins," *Eur. J. Biochem.* 223:141-146, Blackwell Science Ltd. (1994).

Monkarsh, S.P., et al., "Positional Isomers of Monopegylated Interferon α-2a: Isolation, Characterization, and Biological Activity," *Analytical Biochemistry* 247:434-440, Academic Press (1997).

Montalbini, P., et al., "Uricase from leaves: its purification and characterization from three different higher plants," *Planta* 202:277-283, Springer-Verlag (Jun. 1997).

Moore, W.V. and Leppert, P., "Role of Aggregated Human Growth Hormone (hGH) in Development of Antibodies to hGH," *J. Clin. Endocrinol. Metab.* 51:691-697, The Endocrine Society (1980).

Nishida, Y., et al., "Hypouricaemic effect after oral administration in chickens of polyethylene glycol-modified uricase entrapped in liposomes," *J. Pharm. Pharmacol.* 36:354-355, Pharmaceutical Press (1984).

Nishimura, H., et al., "Modification of Yeast Uricase with Polyethylene Glycol: Disappearance of Binding Ability towards Anti-Uricase Serum," *Enzyme* 24:261264, Karger (1979).

Nishimura, H., et al., "Improved Modification of Yeast Uricase with Polyethylene Glycol, Accompanied with Nonimmunoreactivity Towards Anti-Uricase Serum and High Enzymic Activity," *Enzyme* 26:49-53, Karger (1981).

Nucci, M.L., et al., "The Therapeutic Value of Poly(Ethylene Glycol)-Modified Proteins," *Adv. Drug Deliv. Rev.* 6:133-151, Elsevier Science Publishers (1991).

Osman, A.M., et al., "Liver Uricase in *Camelus dromedarius*: Purification and Properties," *Comp. Biochem. Physiol.* 94B:469-474, Pergamon Press Plc. (1989).

Palleroni, A.V., et al., "Interferon Immunogenicity: Preclinical Evaluation of Interferon-α2a," *J. Interferon Cyto. Res.* 17:S23-S27, Mary Ann Liebert, Inc. (Jul. 1997).

"PEG-uricase BioTechnology General, Duke University, Mountain View licensing agreement," *R&D Focus Drug News*, Accession No. 1998:2984, available on Datastar File IPNR/IPNA, (Aug. 1998).

Porstmann, B., et al., "Comparison of Chromogens for the Determination of Horseradish Peroxidase as a Marker in Enzyme Immunoassay," *J. Clin. Chem. Clin. Biochem.* 19:435-439, Walter de Gruyter & Co. (1981).

Pui, C.-H., et al., "Urate oxidase in prevention and treatment of hyperuricemia associated with lymphoid malignancies," *Leukemia* 11:1813-1816, Stockton Press (Nov. 1997).

Saifer, M.G.P., et al., "Plasma Clearance and Immunologic Properties of Long-Acting Superoxide Dismutase Prepared Using 35,000 to 120,000 Dalton Poly-Ethylene Glycol," in: *Free Radicals in Diagnostic Medicine*, Armstrong, D., ed., Plenum Press, New York, NY, pp. 377-387 (1994).

Saifer, M.G.P., et al., "Improved Conjugation of Cytokines Using High Molecular Weight Poly(ethylene glycol): PEG-GM-CSF as a Prototype," *Polymer Prepr.* 38:576-577, American Chemical Society (Apr. 1997).

Sartore, L., et al., "Enzyme Modification by MPEG with an Amino Acid or Peptide as Spacer Arms," *Appl. Biochem. Biotechnol.* 27:45-54, Humana Press (1991).

Savoca, K.V., et al., "Induction of Tolerance in Mice by Uricase and Monomethoxypolyethylene Glycol-Modified Uricase," *Int. Archs. Allergy appl. Immun.* 75:58-67, Karger (1984).

Shearwater Polymers Inc., "Functionalized Biocompatible Polymers for Research and Pharmaceuticals," in: *Shearwater Polymers, Inc., Catalog*, pp. 27, 47, and 48. (Jul. 1997).

Sherman, M.R., et al., "Conjugation of High-Molecular Weight Poly(ethylene glycol) to Cytokines: Granulocyte-Macrophage Colony-Stimulating Factors as Model Substrates," in: *ACS Symposium Series 680. Poly(ethylene glycol). Chemistry and Biological Applications*, Harris, J.M. and Zalipsky, S., eds., American Chemical Society, Washington, DC, pp. 155-169 (Apr. 1997).

Somack, R., et al., "Preparation of Long-Acting Superoxide Dismutase Using High Molecular Weight Polyethylene Glycol (41,000-72,000 Daltons)," *Free Rad. Res. Comms.* 12-13:553-562, Harwood Academic Publishers GmbH (1991).

Suzuki, H. and Verma, D.P.S., "Soybean Nodule-Specific Uricase (Nodulin-35) Is Expressed and Assembled into a Functional Tetrameric Holoenzyme in *Escherichia coli*," *Plant Physiol.* 95:384-389, American Society of Plant Physiologists (1991).

Treuheit, M.J., et al., "Inverse Relationship of Protein Concentration and Aggregation," *Pharm. Res.* 19:511-516, Plenum Publishing Corporation (Apr. 2002).

Tsuji, J.-I., et al., "Studies on Antigenicity of the Polyethylene Glycol (PEG)-Modified Uricase," *Int. J. Immunopharmacol.* 7:725-730, Elsevier Science (1985).

Venkataseshan, V.S., et al., "Acute Hyperuricemic Nephropathy and Renal Failure after Transplantation," *Nephron* 56:317-321, Karger AG (1990).

Veronese, F.M., et al., "Surface Modification of Proteins. Activation of Monomethoxy-Polyethylene Glycols by Phenylchloroformates and Modification of Ribonuclease and Superoxide Dismutase," *Appl. Biochem. Biotechnol.* 11:141-152, The Humana Press, Inc. (1985).

Veronese, F.M., et al., "New Synthetic Polymers for Enzyme and Liposome Modification," in: *ACS Symposium Series 680, Poly(Ethylene Glycol) Chemistry and Biological Applications*, Harris, J.M., and Zalipsky, S., eds., American Chemical Society, Washington, D.C., pp. 182-192 (Apr. 1997).

Wallrath, L.L., et al., "Molecular Characterization of the *Drosophila melanogaster* Urate Oxidase Gene, an Ecdysone-Repressible Gene Expressed Only in the Malpighian Tubules," *Molec. Cell. Biol.* 10:5114-5127, American Society for Microbiology (1990).

Wang, X., et al., "Rat urate oxidase: cloning and structural analysis of the gene and 5'-flanking region," *Gene* 97:223-229, Elsevier Science Publishers B.V. (1991).

Wu, X., et al., "Urate oxidase: Primary structure and evolutionary implications," *Proc. Natl. Acad. Sci.* USA 86:9412-9416, National Academy of Sciences (1989).

Wu, X., et al., "Two Independent Mutational Events in the Loss of Urate Oxidase during Hominoid Evolution," *J. Mol. Evol.* 34:78-84, Springer-Verlag (1992).

Wu, X., et al., "Hyperuricemia and urate nephropathy in urate oxidase-deficient mice," *Proc. Natl. Acad. Sci.* USA 91:742-746, National Academy of Sciences (1994).

Yasuda, Y., et al., "Biochemical and Biopharmaceutical Properties of Macromolecular Conjugates of Uricase with Dextran Polyethylene Glycol," *Chem. Pharm. Bull.* 38:2053-2056, Pharmaceutical Society of Japan (1990).

Yeldandi, A.V., et al., "Human Urate Oxidase Gene: Cloning and Partial Sequence Analysis Reveal a Stop Codon within the Fifth Exon," *Biochem. Biophys. Res. Commun.* 171:641-646, Academic Press (1990).

U.S. Trademark Registration No. 2,246,623, entitled "Puricase," filed Jul. 15, 1997.

Esp@cenet database, Unverified English language abstract for JP 09-154581 (Document FP6).

NCBI Entrez, GenBank Report, Accession No. NP_446220, Wang, X.D., et al. (Oct. 2004).

Co-pending U.S. Appl. No. 11/833,590, inventor Williams et al., filed Aug. 3, 2007.

Office Action mailed on Apr. 6, 2001; in related U.S. Appl. No. 09/501,730, Sherman et al., filed Feb. 10, 2000, now U.S. Patent No. 6,783,965.

Office Action mailed on Dec. 5, 2001; in related U.S. Appl. No. 09/501,730, Sherman et al., filed Feb. 10, 2000, now U.S. Patent No. 6,783,965.

Office Action mailed on May 22, 2002; in related U.S. Appl. No. 09/501,730, Sherman et al., filed Feb. 10, 2000, now U.S. Patent No. 6,783,965.

Office Action mailed on Dec. 3, 2002; in related U.S. Appl. No. 09/501,730, Sherman et al., filed Feb. 10, 2000, now U.S. Patent No. 6,783,965.

Office Action mailed on Jun. 18, 2003; in related U.S. Appl. No. 09/501,730, Sherman et al., filed Feb. 10, 2000, now U.S. Patent No. 6,783,965.
Advisory Action mailed on Nov. 17, 2003; in related U.S. Appl. No. 09/501,730, Sherman et al., filed Feb. 10, 2000, now U.S. Patent No. 6,783,965.
Notice of Allowability mailed on Jan. 13, 2004; in related U.S. Appl. No. 09/501,730, Sherman et al., filed Feb. 10, 2000, now U.S. Patent No. 6,783,965.
Office Action mailed on Feb. 10, 2004; in related U.S. Appl. No. 09/501,730, Sherman et al., filed Feb. 10, 2000, now U.S. Patent No. 6,783,965.
Supplemental Notice of Allowability mailed on Feb. 24, 2004; in related U.S. Appl. No. 09/501,730, Sherman et al., filed Feb. 10, 2000, now U.S. Patent No. 6,783,965.
Office Action mailed on Apr. 9, 2007; in related U.S. Appl. No. 10/928,370, Sherman et al., filed August 30, 2004.
Chinese Second Office Action for Chinese Application No. 01807750.1, issued Mar. 21, 2008, Chinese Patent Office, Beijing, China.
Montalbini, P., et al., "Isolation and characterization of uricase from bean leaves and its comparison with uredospore enzymes," *Plant Sci.* 147:139-147, Elsevier Science Ireland Ltd. (May 1999).
Dialog File 351, Accession No. 8448552, Unverified WPI English language abstract for DD 279486, published Jun. 6, 1990 (Document FP3, submitted in IDS filed Nov. 1, 2007).
"E.C. 1.7.3.3., urate oxidase," BRENDA Enzyme Database, available via internet at www.brenda.uni-koeln.de/ U.S. Appl. No. 09/501,730, filed Feb. 10, 2000.
Esp@cenet database, Unverified English language abstract for JP 09-154581, published Jun. 17, 1997 (Document FP6, submitted in IDS filed Nov. 1, 2007).
Patent Abstracts of Japan, Unverified English language abstract for JP 55-099189, published Jul. 28, 1980 (Document FP1, submitted in IDS filed Nov. 1, 2007).
Patent Abstracts of Japan, Unverified English language abstract for JP 62-055079, published Mar. 10, 1987 (Document FP2, submitted in IDS filed Nov. 1, 2007).
Patent Abstracts of Japan, Unverified English language abstract for JP 03-148298, published Jun. 25, 1997 (Document FP4, submitted in IDS filed Nov. 1, 2007).
Bossavy, J., et al., "Comparison of the Antithrombotic Effect of PEG-Hirudin and Heparin in a Human Ex Vivo Model of Arterial Thrombosis," *Arterioscler. Thromb. Vase. Biol.* 19:1348-1353, American Heart Association, United States (1999).
Clark, R., et al., "Long-acting Growth Hormone Produced by Conjugation with Polyethylene Glycol," *J. Biol. Chem.* 271:21969-21977, The American Society of Biochemistry and Molecular Biology, Inc., United States (1996).
Gaertner, H., and Offord, R., "Site-Specific Attachment of Functionalized Poly(ethylene glycol) to the Amino Terminus of Proteins," *Bioconjugate Chem.* 7:38-44, American Chemical Society, United States (1996).
Hinds, et al., "Synthesis and Characterization of poly(ethylene glycol)-insuline conjugates," *Bioconjugate Chem.* 11:195-201, American Chemical Society, United States (2000).
Inada, Y., et al., "Biomedical and biotechnological applications of PEG- and PM-modified proteins," *Trends Biotechnol.* 13:86-91, Elsevier Science, Ltd., Netherlands (1995).
Kinstler, O., et al., "Characterization and Stability of N-terminally PEGylated rhG-CSF," *Pharm. Res.* 13:996-1002, Plenum Publishing Corporation, United States (1996).
Konstek, et al., "Forty years of interferon," *Acta Virologica* 41:349-353, Slovak Academic Press, Slovak Republic (1997).
Motojima, K., et al., "Cloning and Sequence Analysis of cDNA for Rat Liver Uricase," *J. Biol. Chem.* 263:16677-16681, American Society for Biochemistry and Molecular Biology, Inc., United States (1988).
Sakane, T., and Pardridge, W., "Carboxyl-directed Pegylation of Brain-derived Neurotrophic Factor Markedly Reduces Systemic Clearance with Minimal Loss of Biologic Activity," *Pharm. Res.* 14:1085-1091, Plenum Publishing Corporation, United States (1997).

Sigma Catalog (1993), p. 1002, Product Nos. U 3250, 292-8, U3500, U 9375 or U 3377.
Office Action mailed on Apr. 9, 2007, in U.S. Appl. No. 10/928,370, inventors Sherman et al., filed Aug. 30, 2004.
Office Action mailed on Nov. 2, 2007, in U.S. Appl. No. 10/928,370, inventors Sherman et al., filed Aug. 30, 2004.
Office Action mailed on Sep. 30, 2008, in U.S. Appl. No. 10/928,370, inventors Sherman et al., filed Aug. 30, 2004.
Office Action mailed on Jun. 22, 2009, in U.S. Appl. No. 10/928,370, inventors Sherman et al., filed Aug. 30, 2004.
Office Action mailed on Dec. 9, 2009, in U.S. Appl. No. 10/928,370, inventors Sherman et al., filed Aug. 30, 2004.
Office Action mailed on Aug. 5, 2010, in U.S. Appl. No. 10/928,370, inventors Sherman et al., filed Aug. 30, 2004.
Office Action mailed on Mar. 21, 2001, in U.S. Appl. No. 09/370,084, inventors Williams et al., filed Aug. 6, 1999; now U.S. Patent No. 6,576,235.
Office Action mailed on May 21, 2001, in U.S. Appl. No. 09/370,084, inventors Williams et al., filed Aug. 6, 1999; now U.S. Patent No. 6,576,235.
Office Action mailed on May 29, 2002, in U.S. Appl. No. 09/370,084, inventors Williams et al., filed Aug. 6, 1999; now U.S. Patent No. 6,576,235.
Notice of Allowability mailed on Jan. 13, 2003, in U.S. Appl. No. 09/370,084, inventors Williams et al., filed Aug. 6, 1999; now U.S. Patent No. 6,576,235.
Office Action mailed on Jun. 10, 2003, in U.S. Appl. No. 09/839,946, inventors Williams et al., filed Apr. 19, 2001; now U.S. Patent No. 7,723,089.
Office Action mailed on Sep. 11, 2003, in U.S. Appl. No. 09/839,946, inventors Williams et al., filed Apr. 19, 2001; now U.S. Patent No. 7,723,089.
Office Action mailed on Mar. 5, 2004, in U.S. Appl. No. 09/839,946, inventors Williams et al., filed Apr. 19, 2001; now U.S. Patent No. 7,723,089.
Office Action mailed on Aug. 2, 2004, in U.S. Appl. No. 09/839,946, inventors Williams et al., filed Apr. 19, 2001; now U.S. Patent No. 7,723,089.
Advisory Action mailed on Dec. 20, 2005, in U.S. Appl. No. 09/839,946, inventors Williams et al., filed Apr. 19, 2001; now U.S. Patent No. 7,723,089.
Office Action mailed on Jan. 26, 2005, in U.S. Appl. No. 09/839,946, inventors Williams et al., filed Apr. 19, 2001; now U.S. Patent No. 7,723,089.
Office Action mailed on Jul. 20, 2005, in U.S. Appl. No. 09/839,946, inventors Williams et al., filed Apr. 19, 2001; now U.S. Patent No. 7,723,089.
Notice of Hearing mailed on May 15, 2007, in U.S. Appl. No. 09/839,946, inventors Williams et al., filed Apr. 19, 2001; now U.S. Patent No. 7,723,089.
BPAI Decision mailed on Jul. 18, 2007, in U.S. Appl. No. 09/839,946, inventors Williams et al., filed Apr. 19, 2001; now U.S. Patent No. 7,723,089.
Office Action mailed on Jul. 23, 2008, in U.S. Appl. No. 09/839,946, inventors Williams et al., filed Apr. 19, 2001; now U.S. Patent No. 7,723,089.
Office Action mailed on Aug. 11, 2008, in U.S. Appl. No. 09/839,946, inventors Williams et al., filed Apr. 19, 2001; now U.S. Patent No. 7,723,089.
Office Action mailed on Jan. 2, 2009, in U.S. Appl. No. 09/839,946, inventors Williams et al., filed Apr. 19, 2001; now U.S. Patent No. 7,723,089.
Office Action mailed on May 11, 2009, in U.S. Appl. No. 09/839,946, inventors Williams et al., filed Apr. 19, 2001; now U.S. Patent No. 7,723,089.
Office Action mailed on Oct. 16, 2009, in U.S. Appl. No. 09/839,946, Williams et al., filed Apr. 19, 2001; now U.S. Patent No. 7,723,089.
Notice of Allowability mailed on Dec. 23, 2009, in U.S. Appl. No. 09/839,946, inventors Williams et al., filed Apr. 19, 2001; now U.S. Patent No. 7,723,089.

Office Action mailed on Mar. 22, 2010, in U.S. Appl. No. 11/833,590, inventors Williams et al., filed Aug. 3, 2007.
Co-pending U.S. Appl. No. 12/769,570, filed Apr. 28, 2010, United States Patent Office, Alexandria, VA., United States.
Co-pending U.S. Appl. No. 12/769,572, filed Apr. 28, 2010, United States Patent Office, Alexandria, VA., United States.

Pitts, O., et al., "Uricase: Subunit Composition and Resistance to Denaturants," *Biochem.* 13:888-892, American Chemical Society, United States (1974).
Tla, S., et al., "Urate oxidase from pig liver: biochemical and immunological properties," *Prikl Biokhim Mikrobiol* 14:533-542, Izdatelstvo Nauka, Russia (1978).

SEQUENCE LISTING

```
<160> NUMBER OF SEQ ID NOS: 3

<210> SEQ ID NO 1
<211> LENGTH: 304
<212> TYPE: PRT
<213> ORGANISM: Sus scrofa

<400> SEQUENCE: 1

Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220
```

```
Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
            245                 250                 255

Glu Ile Ser Leu Pro Asn Ile His Tyr Leu Asn Ile Asp Met Ser Lys
        260                 265                 270

Met Gly Leu Ile Asn Lys Glu Glu Val Leu Leu Pro Leu Asp Asn Pro
    275                 280                 285

Tyr Gly Arg Ile Thr Gly Thr Val Lys Arg Lys Leu Thr Ser Arg Leu
290                 295                 300
```

<210> SEQ ID NO 2
<211> LENGTH: 304
<212> TYPE: PRT
<213> ORGANISM: Papio hamadryas

<400> SEQUENCE: 2

```
Met Ala Asp Tyr His Asn Asn Tyr Lys Lys Asn Asp Glu Leu Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Ala Phe Gly Val Asn Ile Cys Glu
                85                  90                  95

Tyr Phe Leu Ser Ser Phe Asn His Val Ile Arg Ala Gln Val Tyr Val
            100                 105                 110

Glu Glu Ile Pro Trp Lys Arg Leu Glu Lys Asn Gly Val Lys His Val
        115                 120                 125

His Ala Phe Ile His Thr Pro Thr Gly Thr His Phe Leu Glu Val Glu
    130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Lys Pro Glu Val Lys Asp Arg Cys Phe Ala Thr Gln
            180                 185                 190

Val Tyr Cys Lys Trp Arg Tyr His Gln Cys Arg Asp Val Asp Phe Glu
        195                 200                 205

Ala Thr Trp Gly Thr Ile Arg Asp Leu Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```

```
<210> SEQ ID NO 3
<211> LENGTH: 304
<212> TYPE: PRT
<213> ORGANISM: Artificial Sequence
<220> FEATURE:
<223> OTHER INFORMATION: Chimera of Sus scrofa and Papio hamadryas

<400> SEQUENCE: 3

Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300
```

AGGREGATE-FREE URATE OXIDASE FOR PREPARATION OF NON-IMMUNOGENIC POLYMER CONJUGATES

CROSS-REFERENCE TO RELATED APPLICATIONS

This application is a continuation of U.S. application Ser. No. 10/928,370, filed Aug. 30, 2004, which is a continuation of U.S. application Ser. No. 09/501,730, filed Feb. 10, 2000 (now U.S. Pat. No. 6,783,965) and is a continuation-in-part of U.S. application Ser. No. 09/839,946, filed Apr. 19, 2001 (now U.S. Pat. No. 7,723,089), which is a divisional of U.S. application Ser. No. 09/370,084, filed Aug. 6, 1999 (now U.S. Pat. No. 6,576,235), which claims the benefit of U.S. Provisional Appl. No. 60/219,318, filed Aug. 6, 1998 (now expired), the disclosures of all of which applications are incorporated herein by reference in their entireties.

STATEMENT OF GOVERNMENT RIGHTS IN THE INVENTION

A portion of the research described in this application was made with support from the U.S.-Israel Binational Industrial Research and Development Foundation. Accordingly, the U.S. Government may have certain rights in the invention.

REFERENCE TO A SEQUENCE LISTING SUBMITTED ELECTRONICALLY VIA EFS-WEB

The content of the electronically submitted sequence listing (Name: Substitute Sequence Listing.ascii.txt, Size: 8,639 bytes; and Date of Creation: Jun. 5, 2009) is herein incorporated by reference in its entirety.

BACKGROUND OF THE INVENTION

1. Field of the Invention

The present invention relates to purification and chemical modification of proteins to prolong their circulating lifetimes and reduce their immunogenicity. More specifically, the invention relates to the removal of aggregates larger than octamers from urate oxidases (uricases) prior to conjugation of poly(ethylene glycols) or poly(ethylene oxides). This substantially eliminates uricase immunogenicity without compromising its uricolytic activity.

2. Description of the Related Art

Statements contained in this background section do not constitute an admission of prior art, but instead reflect the inventors' own subjective comments on and interpretations of the state of the art at the time the invention was made. These interpretations may include personal, heretofore undisclosed, insights of the inventors, which insights were not themselves part of the prior art.

Urate oxidases (uricases; E.C. 1.7.3.3) are enzymes that catalyze the oxidation of uric acid to a more soluble product, allantoin, a purine metabolite that is more readily excreted. Humans do not produce enzymatically active uricase, as a result of several mutations in the gene for uricase acquired during the evolution of higher primates. Wu, X, et al., (1992) *J Mol Evol* 34:78-84. As a consequence, in susceptible individuals, excessive concentrations of uric acid in the blood (hyperuricemia) and in the urine (hyperuricosuria) can lead to painful arthritis (gout), disfiguring urate deposits (tophi) and renal failure. In some affected individuals, available drugs such as allopurinol (an inhibitor of uric acid synthesis) produce treatment-limiting adverse effects or do not relieve these conditions adequately. Hande, K R, et al., (1984) *Am J Med* 76:47-56; Fam, AG, (1990) *Baillière's Clin Rheumatol* 4:177-192. Injections of uricase can decrease hyperuricemia and hypeiuricosuria, at least transiently. Since uricase is a foreign protein in humans, however, even the first injection of the unmodified protein from *Aspergillus flavus* has induced anaphylactic reactions in several percent of treated patients (Pui, C-H. et al., (1997) *Leukemia* 11:1813-1816), and immunologic responses limit its utility for chronic or intermittent treatment. Donadio, D, et al., (1981) *Nouv Presse Méd* 10:711-712; Leaustic, M, et al., (1983) *Rev Rhum Mal Osteoartic* 50553-554.

U.S. patent application Ser. No. 09/370,084 (now U.S. Pat. No. 6,576,235) and published International Application No. PCT/US99/17514 (now abandoned), the entire contents of which are incorporated herein by reference, disclose poly (ethylene glycol)-urate oxidase (PEG-uricase) that retains at least about 75% of the uricolytic activity of unconjugated uricase and has substantially reduced immunogenicity. In one such purified uricase, each subunit is covalently linked to an average of 2 to 10 strands of PEG, wherein each molecule of PEG may have a molecular weight between about 5 kDa and 100 kDa.

The aggregation of proteins is known to increase their immunogenicity. This understanding has contributed to the development of methods for intentionally aggregating proteins by treatments such as thermal denaturation and cross-linking by exposure to glutaraldehyde prior to use in the preparation of vaccines or for immunization of animals to produce antisera.

Unintentional aggregation of proteins has also been recognized as contributing to immunization or sensitization during clinical use of therapeutic proteins, e.g. for human gamma globulin (Henney et al. (1968) *N. Engl. J. Med.* 278:2244-2246) and for human growth hormone (Moore et al. (1980) *J. Clin. Endocrinol. Metab.* 51:691-97). The contribution of aggregates to the immunogenicity of human interferon alpha has been demonstrated in BALB/c mice (Braun et al. (1997) *Pharm. Res.* 14:1472-1478) and an enzyme-linked immunosorbent assay (ELISA) has been developed for their measurement (Braun et al. (1997) *Pharm. Res.* 14:1394-1400).

In contrast to the known effects of aggregation on the immunogenicity of proteins, there are not reports of the effect of aggregation on the immunogenicity of proteins conjugated to poly(alkylene glycols) such as PEG. There is a need for poly(allylene glycol)-uricase conjugates that substantially eliminates uricase immunogenicity without compromising its uricolytic activity. The present invention provide such compositions.

SUMMARY OF THE INVENTION

Conjugation of proteins with poly(alkylene glycols), especially PEG, produces conjugates with reduced immunogenicity and increased persistence in the bloodstream. In attempting to produce substantially non-immunogenic conjugates of uricase that retain substantially all of the uricolytic activity of the unmodified uricase preparation, it was discovered that traces of large aggregates of uricase in the starting material were surprisingly effective at provoking both antibody formation and accelerated clearance from the circulation, both of which are deleterious, after repeated injections of PEG conjugates prepared from uricase containing such aggregates. Surprisingly, the present inventors found that the increased immunogenicity and accelerated clearance were not due to the presence of well-defined, moderate-sized aggregates of the uricase subunit that are larger than the native tetramer, e.g.

aggregates containing eight subunits (octamers). The octameric form of uricase is present at sufficiently high concentrations in most preparations of uricase to Abe detectable by its absorbance of UV light, e.g. at 214 nm or 276 nm, or by its contribution to the refractive index or other measurements of protein concentration. Nevertheless, the octamers themselves were found to contribute minimally to the immunogenicity and accelerated clearance of PEG-uricase conjugates, in contrast with the much smaller quantities of the much larger aggregates that are undetectable by UV absorbance under the conditions tested but are readily detected by static (Raleigh) or dynamic light scattering. Therefore, the removal of such traces of very large aggregates prior to conjugation with PEG was found to decrease the immunogenicity and the accelerated clearance of the resultant PEG-uricase conjugates to a surprising extent.

One embodiment of the present invention is purified urate oxidase (uricase) substantially free of aggregates larger than octamers. Preferably, the uricase is mammalian uricase. More preferably, the uricase is porcine liver, bovine liver or ovine liver uricase. In one aspect of this preferred embodiment, the uricase is recombinant. In another aspect of this preferred embodiment, the uricase has substantially the sequence of porcine, bovine, ovine or baboon liver uricase. Advantageously, the uricase is chimeric. Preferably, the uricase is, PKS uricase. In another aspect of this preferred embodiment, the uricase has substantially the sequence of baboon liver uricase in which tyrosine 97 has been replace by histidine. Preferably, the uricase comprises an amino terminus and a carboxy terminus, and wherein the uricase is truncated at one terminus or both termini. Advantageously, the uricase is a fungal or microbial uricase. Preferably, the fungal or microbial uricase is; isolated from *Aspergillus flavus, Arthrobacter globiformis, Bacillus* sp. or *Candida utilis*, or is a recombinant enzyme having substantially the sequence of one of said uricases. Alternatively, the uricase is an invertebrate uricase. Preferably, the invertebrate uricase is isolated from *Drosophila melanogaster* or *Drosophia pseudoobscura*, or is a recombinant enzyme having substantially the sequence of one of said uricases. In another aspect of this preferred embodiment, the uricase is a plant uricase. Preferably, the plant uricase is isolated from root nodules of *Glycine max* or is a recombinant enzyme having substantially the sequence of the uricase.

In one aspect of this preferred embodiment, the uricase described above is conjugated to poly(ethylene glycol) or poly(ethylene oxide), under conditions such that the uricase in the conjugate is substantially free of aggregates larger than octamers. Preferably, the uricase is conjugated to poly(ethylene glycol) or poly(ethylene oxide) via a urethane (carbamate), secondary amine or amide linkage. In one aspect of this preferred embodiment, the poly(ethylene glycol) is monomethoxy poly(ethylene glycol). In another aspect of this preferred embodiment, the poly(ethylene glycol) or poly(ethylene oxide) has a molecular weight between about 5 kDa and 30 kDa. Preferably, the poly(ethylene glycol) or poly(ethylene oxide) has a molecular weight between about 10 kDa and 20 kDa. Advantageously, the average number of strands of said poly(ethylene glycol) or poly(ethylene oxide) is between about 2 and 12 per uricase subunit. More advantageously, the average number of strands of said poly(ethylene glycol) or poly(ethylene oxide) is between about 6 and 10 per uricase subunit. Most advantageously, the average number of strands of said poly(ethylene glycol) or poly(ethylene oxide) is between about 7 and 9 per uricase subunit. Preferably, the poly(ethylene glycol) or poly(ethylene oxide) is linear. Alternatively, the poly(ethylene glycol) or poly(ethylene oxide) is branched.

The present invention also provides a pharmaceutical composition for lowering uric acid levels in a body fluid or tissue, comprising the uricase conjugate described above and a pharmaceutically acceptable carrier. Preferably, the composition is stabilized by lyophilization and dissolves upon reconstitution to provide solutions suitable for parenteral administration.

Another embodiment of the invention is a method for purifying uricase having reduced immunogenicity, comprising the step of separating uricase aggregates larger than octamers in uricase fractions, and excluding such aggregates from the purified uricase. Preferably, the separating step comprises the step of detecting aggregates larger than octamers from at least a portion of the uricase fractions and excluding the fractions containing the aggregates. Advantageously, the detecting step comprises measurement of light scattering.

The present invention also provides isolated uricase prepared by the method described above.

DETAILED DESCRIPTION OF THE PREFERRED EMBODIMENTS

Figure 1:
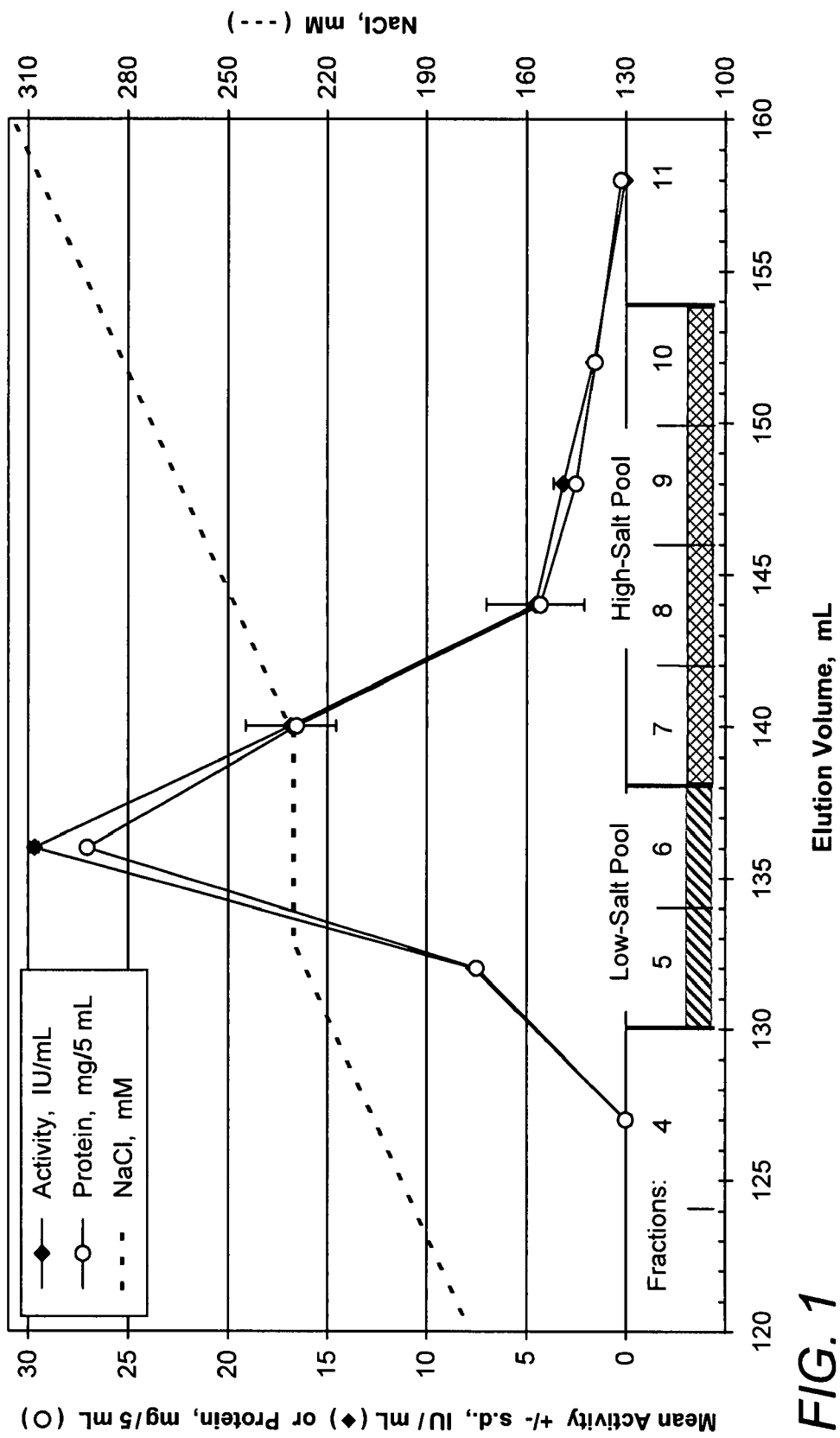
FIG. 1 illustrates uricase activity, total protein and salt concentrations in fractions from a Pharmacia Biotech Mono Q (1×10 cm) anion exchange column. Uricase activity was measured at room temperature by monitoring the decrease in absorbance at 292 nm of 100 µM uric acid in 200 mM sodium borate, pH 9.2. Total protein was determined from the area under the curve of the absorbance peak of uricase in size-exclusion HPLC analyses. Salt concentrations were calculated from the conductivities at room temperature using a standard curve for NaCl in the same buffer.

Previous studies have shown that when a significant reduction in the immunogenicity and/or antigenicity of uricase is achieved by conjugation with PEG (PEGylation), it is invariably associated with a substantial loss of uricolytic activity. The present invention includes the observation that traces of aggregates of urate oxidases larger than octamers substantially contribute to immunogenicity and the induction of accelerated clearance of PEG-uricase conjugates. This discovery is most likely applicable to proteins other than uricases, including interferons and growth factors.

The safety, convenience and cost-effectiveness of biopharmaceuticals are all adversely impacted by decreases in their potencies and the resultant need to increase the administered dose. Thus, there is a need for a safe and effective alternative means for lowering elevated levels of uric acid in body fluids, including blood and urine. The present invention provides a method for producing uricase that excludes uricase aggregates larger than octamers for use in the synthesis of PEG-uricase. This PEG-uricase retains all or nearly all of the uricolytic activity of the unmodified enzyme. The present invention also provides purified uricase substantially free of aggregates larger than octamers. The term "substantially free" indicates that the purified uricase comprises no more than about 2%, and preferably no more than about 1% of aggregates larger than octamers.

The present invention provides a method for purifying uricase such that aggregates larger then octamers are excluded from the purified preparation. Because these larger aggregates are highly immunogenic, their presence in the purified uricase preparation is undesirable. The method involves monitoring column fractions by light scattering rather than or in addition to ultraviolet absorbance at 280 nm, because the aggregates may be too dilute to be detected by ultraviolet absorbance. The purified uricase is then conjugated to water-soluble polymers, preferably poly(ethylene glycols) or poly(ethylene oxides) as described in copending U.S. application Ser. No. 09/370,084, the entire contents of which are incorporated herein by reference.

The removal of aggregated uricase from a preparation consisting predominantly of tetrameric uricase can be accomplished by any of the methods know to those skilled in the art, including size-exclusion chromatography, ion-exchange chromatography, ultrafiltration through a microporous membrane and centrifugation, including ultracentrifugation. The separation method may include separation and analysis of fractions and the rejection or exclusion of those fractions containing excessive quantities of large aggregates. The resultant uricase preparation is better suited for the synthesis of substantially non-immunogenic conjugates of uricase than is the unfractionated uricase. For chronic administration, it is important that PEG conjugares of proteins, e.g. PEG-uricase, have low immunogenicity and do not provoke progressively more rapid clearance from the bloodstream after repeated doses.

The invention also provides pharmaceutical compositions of the polymer-uricase conjugates. These conjugates are substantially non-immunogenic and retain at least 75%, preferably 85%, and more preferably 95% or more of the uricolytic activity of the unmodified enzyme. Uricases suitable for conjugation to water-soluble polymers include naturally occurring urate oxidases isolated from bacteria, fungi and the tissues of plants and animals, both vertebrates and invertebrates, as well as recombinant forms of uricase, including mutated, hybrid, and/or truncated enzymatically active variants of uricase. Water-soluble polymers suitable for use in the present invention include linear and branched poly(ethylene glycols) or poly(ethylene oxides), all commonly known as PEGs. Examples of branched PEG are the subject of U.S. Pat. No. 5,643,575. One preferred example of linear PEG is monomethoxyPEG, of the general structure $CH_3O—(CH_2CH_2O)_nH$, where n varies from about 100 to about 2,300.

One embodiment of the present invention is a conjugate of urate oxicase (uricase) that retains at least about 75% of the uricolytic activity of unconjugated uricase and has substantially reduced immunogenicity. The uricase of this aspect of the invention may be recombinant. Whether recombinant or not, the uricase may be of mammalian origin. In one aspect of this embodiment, the uricase may be porcne, bovine or ovine liver uricase. In another aspect of this embodiment, the uricase may be chimeric. The chimeric uricase may contain portions of porcine liver and/or baboon liver uricase. For example, the chimeric uricase may be porcine uricase containing the mutations R291K and T301S (PKS uricase). Alternatively, the uricase may be baboon liver uricase in which tyrosine 97 has been replaced by histidine, whereby the specific activity of the uricase may be increased by at least about 60%. The uricase of the invention, whatever the origin, may also be in a form that is truncated, either at the amino terminal, or at the carboxyl terminal, or at both terminals. Likewise, the uricase may be fungal or microbial uricase. In one aspect of this embodiment, the fungal or microbial uricase may be a naturally occurring or recombinant form of uricase from *Aspergillus flavus, Arthrobacter globiformis, Bacillus* sp. or *Candida uzlis*. Alternatively, the uricase may be an invertebrate uricase, such as, for example, a naturally occurring or recombinant form of uricase from *Drosophila melanogaster* or *Drosophila pseudoobscura*. The uricase of the invention may also be a plant uricase, for example, a naturally occurring or recombinant form of uricase from soybean root nodule (*Glycine max*). The PEG may have an average molecular weight between about 5 kDa and 100 kDa; preferably the PEG may have an average molecular weight between about 8 kDa and 60 kDa; more preferably, the PEG may have an average molecular weight between about 10 kDa and about 40 kDa, such as, for example, 10 to 20 kDa. The average number of covalently coupled strands of PEG may be 2 to 12 strands per uricase subunit; preferably, the average number of covalently coupled strands may be 6 to 10 per subunit; more preferably, the average number of strands of PEG may be 7 to 9 per subunit. In one aspect of this embodiment, the uricase may be tetrameric. The strands of PEG may be covalently linked to uricase via urethane (carbamate) linkages, secondary amine linkages, and/or amide linkages. When the uricase is a recombinant form of any of the uricases mentioned herein, the recombinant form may have substantially the sequence of the naturally occurring form.

One preferred mammalian uricase is recombinant pig-baboon chimeric uricase, composed of portions of the sequences of pig liver and baboon liver uricase, both of which were first determined by Wu, et al., (1989). One example of such a chimeric uricase contains the first 288 amino acids from the porcine sequence (SEQ ID NO: 1) and the last 16 amino acids from the baboon sequence (SEQ ID NO: 2). Since the latter sequence differs from the porcine sequence at only two positions, having a lysine (K) in place of arginine at residue 291 and a serine (S) in place of threonine at residue 301, this mutant is referred to as pig-K-S or PKS uricase (SEQ ID NO: 3). PKS uricase has one more lysine residue and, hence, one more potential site of PEGylation than either the porcine or baboon sequence.

The cDNAs for various mammalian uricases, including PKS uricase, were subcloned and the optimal conditions were defined for expression in *E. coli*, using standard methods. See Erlich, HA, (Ed.) (1989) *PCR Technology. Principles and Applications for DNA Amplification*. New York: Stockton Press; Sambrook, J, et al., (1989) *Molecular Cloning. A Laboratory Manual, Second Edition*. Cold Spring Harbor, N.Y.: Cold Spring Harbor Laboratory Press. The recombinant uricases were extracted, purified and their stability and activity were assessed using a modification of standard assays. See Fridovich, I, (1965) *J Biol Chem* 240:2491-2494; Nishimura, et al., (1979), and Examples 1 and 5.

In one embodiment of the invention, uricase may be conjugated via a biologically stable, nontoxic, covalent linkage to a relatively small number of strands of PEG. Such linkages may include urethane (carbamate) linkages, secondary amine linkages, and amide linkages. Various activated PEGs suitable for such conjugation are available commercially from Shearwater Polymers, Huntsville, Ala.

For example, urethane linkages to uricase may be formed by incubating uricase in the presence of the succinimidyl carbonate (SC) or p-nitrophenyl carbonate (NPC) derivative of PEG. SC-PEG may be synthesized using the procedure described in U.S. Pat. No. 5,612,460, which is hereby incorporated by reference. NPC-PEG may be synthesized by reacting PEG with p-nitrophenyl chloroformate according to methods described in Veronese, F M, et al., (1985) *Appl Biochem Biotechnol* 11:141-152, and in U.S. Pat. No. 5,286,637, which is hereby incorporated by reference. The methods described in the '637 patent are adapted to PEGs of higher molecular weight by adjusting the concentrations of the reactants to maintain similar stoichiometry. An alternative method of synthesis of NPC-PEG is described by Büttner, W, et al., East German Patent Specification DD 279 486 A1.

Amide linkages to uricase may be obtained using an N-hydroxysuccinimide ester of a carboxylic acid derivative of PEG (Shearwater Polymers). Secondary amine linkages may be formed using 2,2,2-trifluoroethanesulfonyl PEG (tresyl PEG; Shearwater Polymers) or by reductive alkylation using PEG aldehyde (Shearwater Polymers) and sodium cyanoborohydride.

In conjugates containing PEG with a molecular weight of 10 kDa, the maximum number of strands of PEG that were coupled per subunit, while retaining at least 75% of the uricolytic activity of the unmodified enzyme, was about 12 strands for mammalian uricases (e.g. PKS uricase, a mutein of porcine uricase; see assay conditions in Example 5). The latter extent of PEGylation corresponds to about 40% of the total amino groups. In one embodiment of the invention, the average number of strands of PEG coupled per uricase subunit is between about 2 and 12. In a preferred embodiment, the average number of strands of PEG coupled per uricase subunit is between about 6 and 10. In a more preferred embodiment, the average number of covalently linked strands of PEG per uricase subunit is between about 7 and 9. In another embodiment, the molecular weight of PEG used for the coupling reaction is between about 5 kDa and 30 kDa, preferably between about 10 kDa and 20 kDa.

There are several factors that may affect the choice of the optimal molecular weight and number of strands of PEG for coupling to a given form of uricase. In general, the reduction or elimination of immunogenicity without substantial loss of uricolytic activity may require the coupling of relatively more strands of PEG of lower molecular weight, compared to relatively fewer strands of PEG of higher molecular weight. Likewise, each different form of uricase may have a different optimum with respect to both the size and number of strands. The optimal number of strands of PEG and PEG molecular weight can be readily determined using the methods described herein.

When PEG conjugates of mammalian uricase were prepared from the purified tetrameric and octameric forms of the enzyme (containing four or eight subunits of approximately 35 kDa), they displayed profoundly reduced immunogenicity in mice, in contrast to the moderate immunogenicity of PEG conjugates of uricase preparations containing large aggregates (see FIG. 6) and the very high immunogenicity of the unmodified enzyme.

Purified preparations of naturally occurring and recombinant uricases usually contain a mixture of very large aggregates of the enzyme, in addition to the tetrameric (140-kDa) and the octameric (280-kDa) forms. The percentage of each uricase preparation that is in either the tetrameric or octameric form generally varies from about 20% to 95% (see FIGS. 2-4). Despite evidence that unPEGylated aggregates of several other proteins are highly immunogenic (see, e.g., Moore, W V, et al., (1980) *J Clin Endocrinol Metab* 51:691-697), previous studies of PEG-uricase do not describe any efforts to limit the content of aggregates, suggesting that the potential immunogenicity of the PEG-modified aggregates was not considered. On the basis of the observations of the present inventor, it appears likely that such aggregates were present in the enzyme preparations used for previous syntheses of PEG-uricase. Their presence may have rendered the task of preparing non-immunogenic conjugates more difficult. It also appears that the large losses of uricolytic activity observed in previous efforts to PEGylate uricase were related to the large number of strands of low molecular weight PEG that were coupled. On the other hand the methods of uricase purification and PEGylation described herein permit the covalent attachment of as many as 12 strands of PEG per subunit while retaining more than 75% of the uricolytic activity, at least for certain uricases, e.g., PKS uricase (a mutein, of porcine uricase) and the enzyme from thermophilic *Bacillus* sp.

In another preferred embodiment, substantially all large aggregates of the enzyme may be removed by ion-exchange chromatography (FIGS. 1-3) or size-exclusion chromatography at a pH between about 9 and 10.5, preferably 10.2, prior to conjugation of the resulting substantially aggregate-free preparation of uricase to PEG. The molecular weight of the uricase in each fraction from the preparative column may be monitored by any size-dependent analytical technique, including, for example, HPLC, conventional size-exclusion chromatography, centrifugation, light scattering, capillary electrophoresis or gel electrophoresis in a non-denaturing buffer. For aggregate-free uricase isolated using size-exclusion chromatography, fractions containing only the 140-kDa and 280-kDa forms of the enzyme may be pooled and used for conjugation to PEG. For tetrameric plus octameric uricase isolated using ion-exchange chromatography, fractions from the ion-exchange column may be analyzed with respect to size to determine which fractions contain substantial amounts of the tetrameric and octameric forms without the large aggregates detected by light scattering. In the purified product, the undesirable large aggregates may thus constitute as little as about 1%, or less, of the total uricase.

Figure 5:
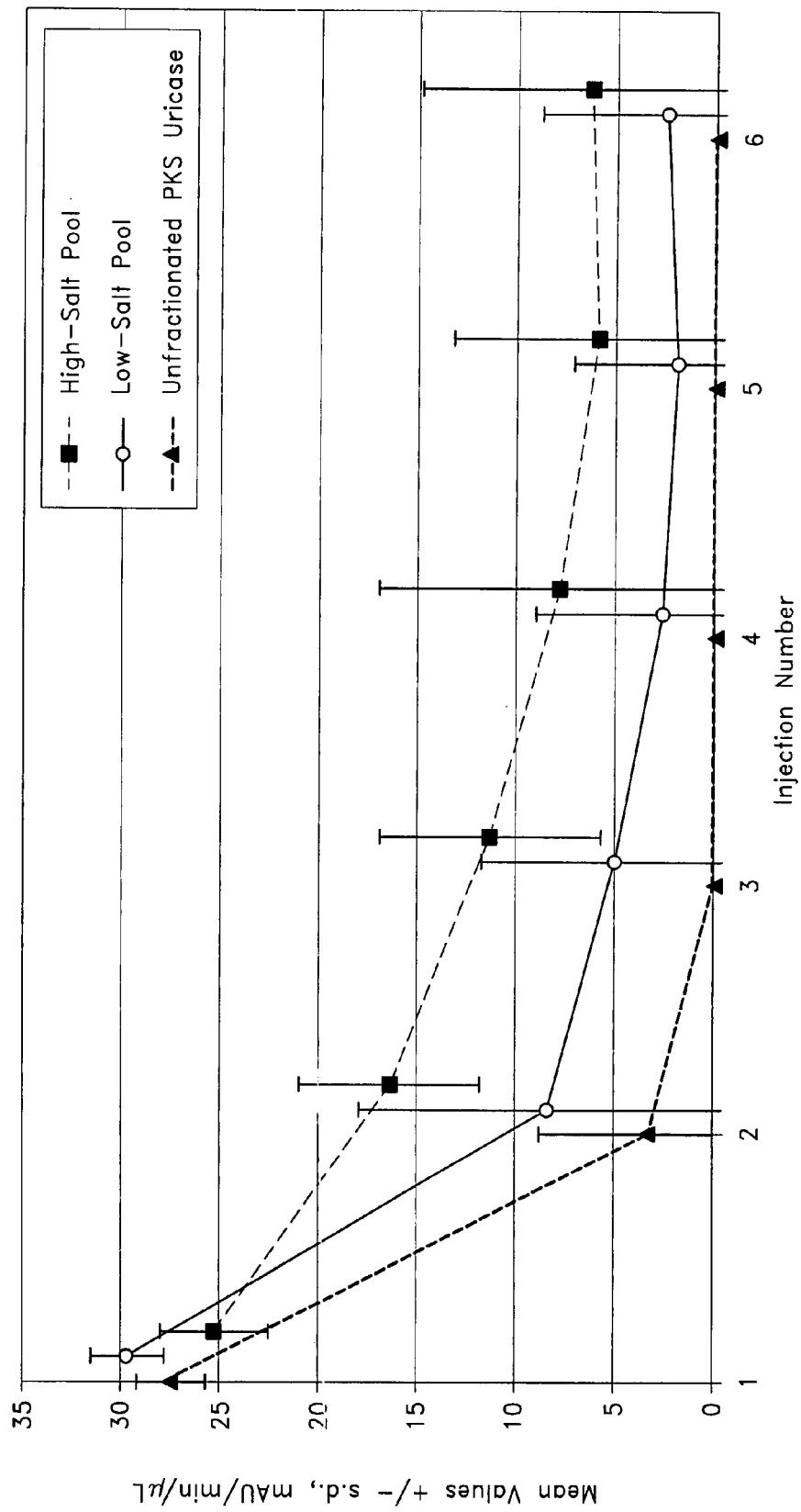
FIG. 5 illustrates TV assays, as in FIG. 1, of uricase activity after a 4-hour incubation at 37° C., in sera drawn 24 hours after each of six weekly injections of 6×10-kDa PEG conjugates of PKS uricase or of pools from Mono Q column fractions.
Figure 6:
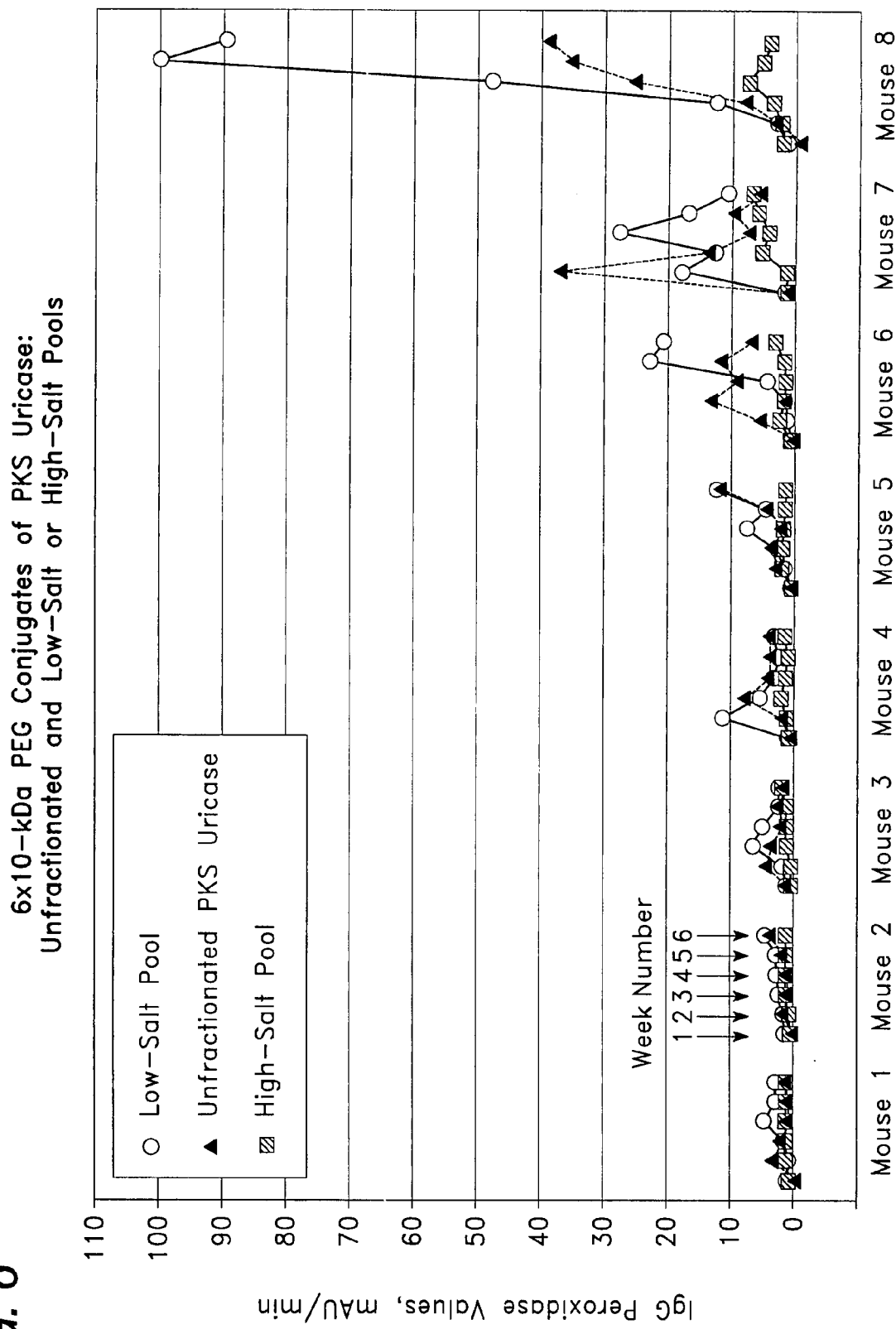
FIG. 6 illustrates ELISA analyses of IgG antibody formation against PEG conjugates of PKS uricase and against PEG conjugates of the pools of fractions from the Mono Q column shown in FIG. 1 in sera drawn 24 hours after each of six weekly injections of female BALB/c mice with 0.2 mg of uricase protein per 20 grams of body weight. For each mouse, data from bleedings 24 hours after the first through sixth injections are shown from left to right. The assay conditions are described in Example 6. Data for the eight mice in each group were arranged in order of increasing immune response, from left to right.

The results presented herein indicate that, even when extensively PEGylated, forms of PKS uricase larger than the octamer provoke accelerated clearance (FIG. 5) and are somewhat immunogenic in mice (FIG. 6). In contrast, conjugates prepared from uricase that is essentially free of large aggregates (detectable by light scattering) could be reinjected at least six times at one-week intervals with much less evidence of accelerated clearance rates (FIG. 5) and without the detectable formation of antibodies, as measured by a sensitive enzyme-linked immunoassay (FIG. 6). The use of highly purified tetrameric or octameric uricase further distinguishes the improved conjugates of the present invention from the PEG-uricase preparations described previously. In contrast, the presence of a significant content of large aggregates in the uricase preparations used by some previous investigators may have led them to couple large numbers of strands of PEG in efforts to suppress the immunogenicity. Consequently, the enzymatic activity of the resultant conjugates was decreased substantially.

The PEG-uricase conjugates of the present invention are useful for lowering the levels of uric acid in the body fluid and tissues of mammals, preferably humans, and can thus be used for treatment of elevated uric acid levels associated with conditions including gout, tophi, renal insufficiency, organ transplantation and malignant disease. PEG-uricase conjugates may be injected into a mammal having excessive uric acid levels by any of a number of routes, including intravenous, subcutaneous, intradermal, intramuscular and intraperitoneal routes. Alternatively, they may be aerosolized and inhaled. See Patton, JS, (1996) *Adv Drug Delivery Rev* 19:3-36 and U.S. Pat. No. 5,458,135'. The effective dose of PEG-uricase of the present invention will depend on the level of uric acid and the size of the individual. In one embodiment of this aspect of the invention PEG-uricase is administered in a pharmaceutically acceptable excipient or diluent is an amount ranging from about 10 µg to about 1 g. In a preferred embodiment, the amount administered is between about 100 µg and 500 mg. More preferably, the conjugated uricase is administered in an amount between 1 mg and 100 mg, such as, for example, 5 mg, 20 mg or 50 mg. Masses given for dosage amounts of the embodiments refer to the amount of protein in the conjugate.

Pharmaceutical formulations containing PEG-uricase can be prepared by conventional techniques, e.g., as described in Gennaro, A R (Ed.) (1990) *Remington's Pharmaceutical Sciences*, 18th Edition, Easton, Pa.: Mack Publishing Co. Suitable excipients for the preparation of injectable solutions include, for example, phosphate buffered saline, lactated Ringer's solution, water, polyols and glycerol. Pharmaceutical compositions for parenteral injection comprise pharmaceutically acceptable sterile aqueous or non-aqueous liquids, dispersions, suspensions, or emulsions as well as sterile powders for reconstitution into sterile injectable solutions or dispersions just prior to use. These formulations may contain additional components, such as, for example, preservatives, solubilizers, stabilizers, wetting agents, emulsifiers, buffers, antioxidants and diluents.

PEG-uricase may also be provided as controlled-release compositions for implantation into an individual to continually control elevated uric acid levels in body fluids. For example, polylactic acid, polyglycolic acid, regenerated collagen, poly-L-lysine, sodium alginate, gellan gum, chitosan, agarose, multilamellar liposomes and many other conventional depot formulations comprise bioerodible or biodegradable materials that can be formulated with biologically active compositions. These materials, when implanted or injected, gradually break down and release the active material to the surrounding tissue. For example, one method of encapsulating PEG-uricase comprises the method disclosed in U.S. Pat. No. 5,653,974, which is hereby incorporated by reference. The use of bioerodible, biodegradable and other depot formulations is expressly contemplated in the present invention. The use of infusion pumps and matrix entrapment systems for delivery of PEG-uricase is also within the scope of the present invention. PEG-uricase may also advantageously be enclosed in micelles or liposomes. Liposome encapsulation technology is well known in the art. See, e.g., Lasic, D, et al., (Eds.) (1995) *Stealth Liposomes*. Boca Raton, Fla.: CRC Press.

The PEG-uricase pharmaceutical compositions of the invention will decrease the need for hemodialysis in patients at high risk of urate-induced renal failure, e.g., organ transplant recipients (see Venkataseshan, V S, et al., (1990) *Nephron* 56:317-321) and patients with some malignant diseases. In patients with large accumulations of crystalline urate (tophi), such pharmaceutical compositions will improve the quality of life more rapidly than currently available treatments.

The following examples, which are not to be construed as limiting the invention in any way, illustrate the various aspects disclosed above. These examples describe PEG-uricases prepared by coupling activated PEG (e.g., the p-nitrophenyl carbonate derivative) to a mutein of porcine uricases. These examples provide guidance to one of ordinary skill in the art for producing substantially non-immunogenic conjugates of uricase that retain at least about 75% of the uricolytic activity of the unmodified enzyme and are well suited for chronic administration.

Example 1

Preparative Ion-Exchange Chromatography of Uricase

Figure 2:
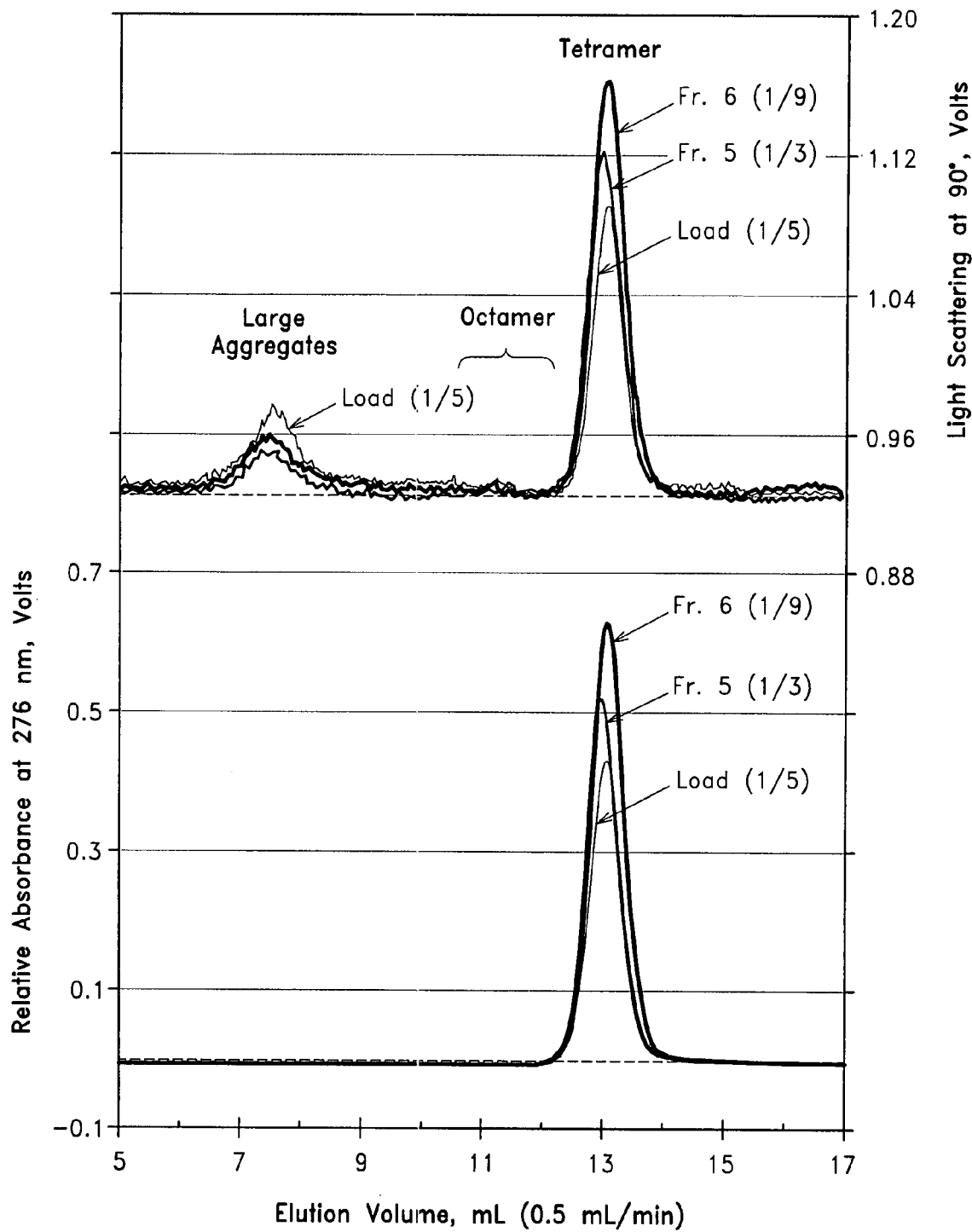
FIG. 2 illustrates size-exclusion HPLC analysis on a Pharmacia Superdex 200 column (1×30 cm) of the load and selected fractions from a preparative Mono Q chromatography of porcine uricase (containing the mutations R291K and T301S (PKS uricase) showing data obtained by a light-scattering detector at 90° C. (upper curves) and by absorbance at 276 nm (lower curves). The different signal strengths of the tetrameric, octameric and more highly aggregated forms of uricase in the unfractionated sample (load) and the various fractions are evident. The load was diluted ⅕ with Mono Q column buffer, fraction 5 was diluted ⅓ and fraction 6 was diluted ⅑. Fractions 5 and 6 were combined to form the "low salt pool."
Figure 3:
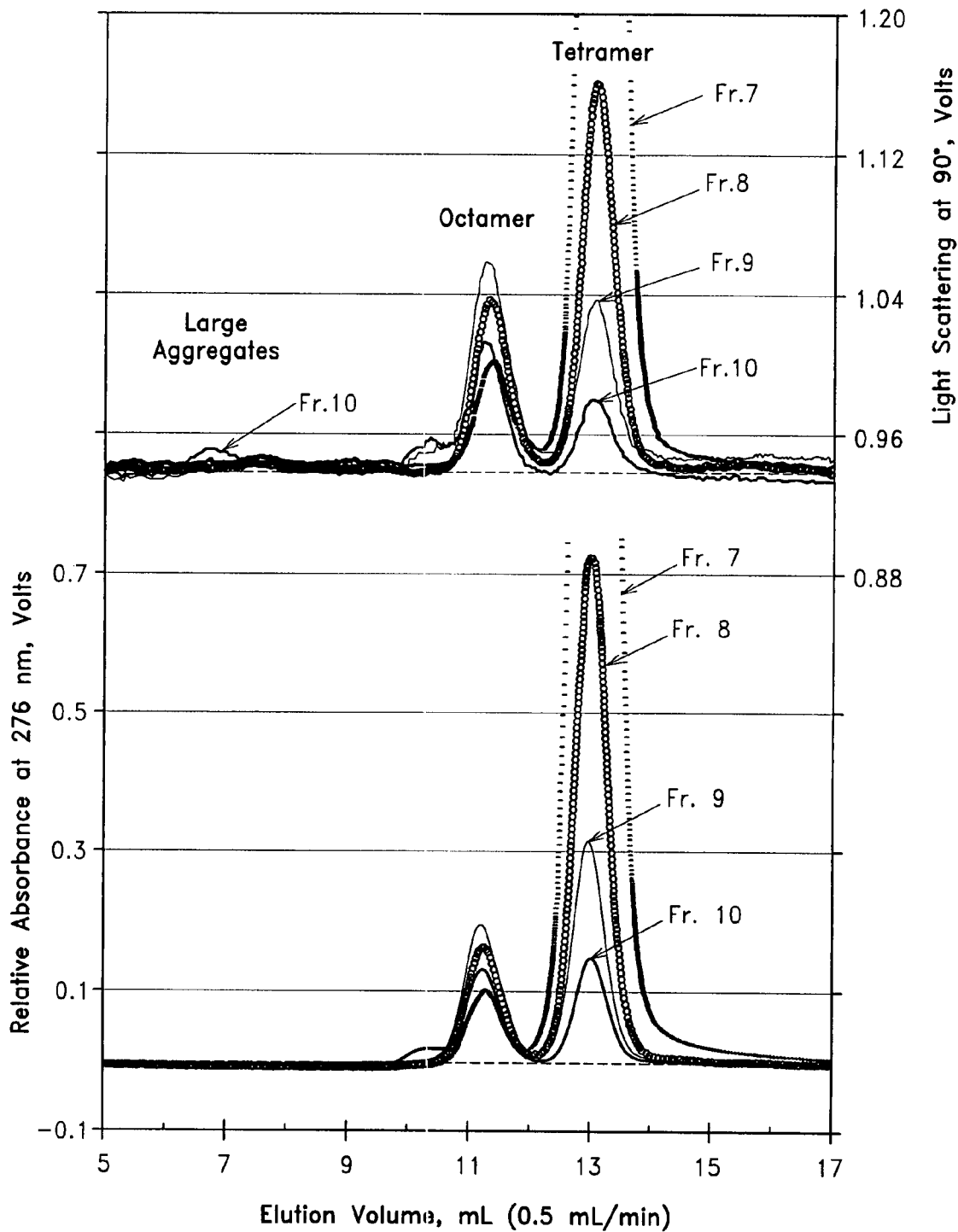
FIG. 3 illustrates size-exclusion analyses of fractions from the Mono Q column in FIG. 1, showing data obtained by a light-scattering detector at 900 and by absorbance at 276 mm, as in FIG. 2. The fractions shown in this figure were used to form the "high salt pool", from which PEG conjugates were prepared and injected into BALB/c mice. The resultant serum activities and immunologic responses in BALB/c mice are shown in FIGS. 5 and 6.

Preparative ion-exchange chromatography was performed on a Fast Protein Liquid Chromatography (FPLC) apparatus (Amersham Pharmacia, Piscataway, N.J.). The Mono Q column (1×10 cm, Amersham Pharmacia) was eluted with a gradient of 50 mM sodium carbonate, pH 10.3, 0.1 M NaCl (Buffer A) to 50 mM sodium carbonate, pH 10.3, 0.6 M NaCl (Buffer B) at a flow rate of 0.5 ml/min except that the sample was loaded at a lower flow-rate. This technique was used to fractionate 25 mL of a solution of PKS uricase (pH 10.3). PKS uricase was obtained from Bio-Technology General Limited (Rehovot, Israel). The latter is recombinant porcine uricase in which one residue of lysine (K) and one residue of serine (S) have replaced one residue of arginine and one residue of threonine, respectively, in the parental porcine sequence (Lee et al. (1988) *Science* 239:1288-1291. Wu et al. (1989) *Proc. Natl. Acad. Sci. U.S.A.* 86::9412-9416). After the sample was loaded, the column was washed with 100 mL of Buffer A. The peak of uricase began to elute at the end of a 31-mL linear gradient of 0 to 26% Buffer B. Most of the uricase was eluted isocratically by 7 mL of buffer containing 26% Buffer B. The remainder of the recovered uricase was eluted by a linear 89-mL gradient of 26% to 100% buffer B. Fractions of 4 mL or 6 mL were collected. Aliquots of Fractions #4-11 were assayed for uricase, total protein and NaCl concentration (FIG. 1) and were analyzed by size-exclusion high performance liquid chromatography (HPLC) as described in Example 2 (FIGS. 2 and 3). The remaining portions of Fractions #5-10 were coupled to PEG, as described in Example 3. Based on the results of the analyses in Example 2, the PEG conjugates of Fractions #5 and 6 were combined as the "Low-Salt Pool" and the PEG conjugates of Fractions #7-10 were combined as the "High-Salt Pool," as indicated in FIG. 1.

Example 2

Size-Exclusion Chromatography of Uricase Monitored by Light Scattering and Ultraviolet Absorbance Size-exclusion HPLC was performed at room temperature on a Superdex 200 column (1×30 cm, Amersham Pharmacia Biotech) on unfractionated PKS uricase and on selected fractions from the preparative Mono Q chromatography of PKS uricase of Example 1. The eluate from the absorbance monitor (UV 2000) of the Thermo Separations HPLC (Sunnyvale, Calif.) was analyzed by light scattering at 90° to the incident light, using a MiniDawn detector from Wyatt Technologies (Santa Barbara, Calif.).

Figure 4:
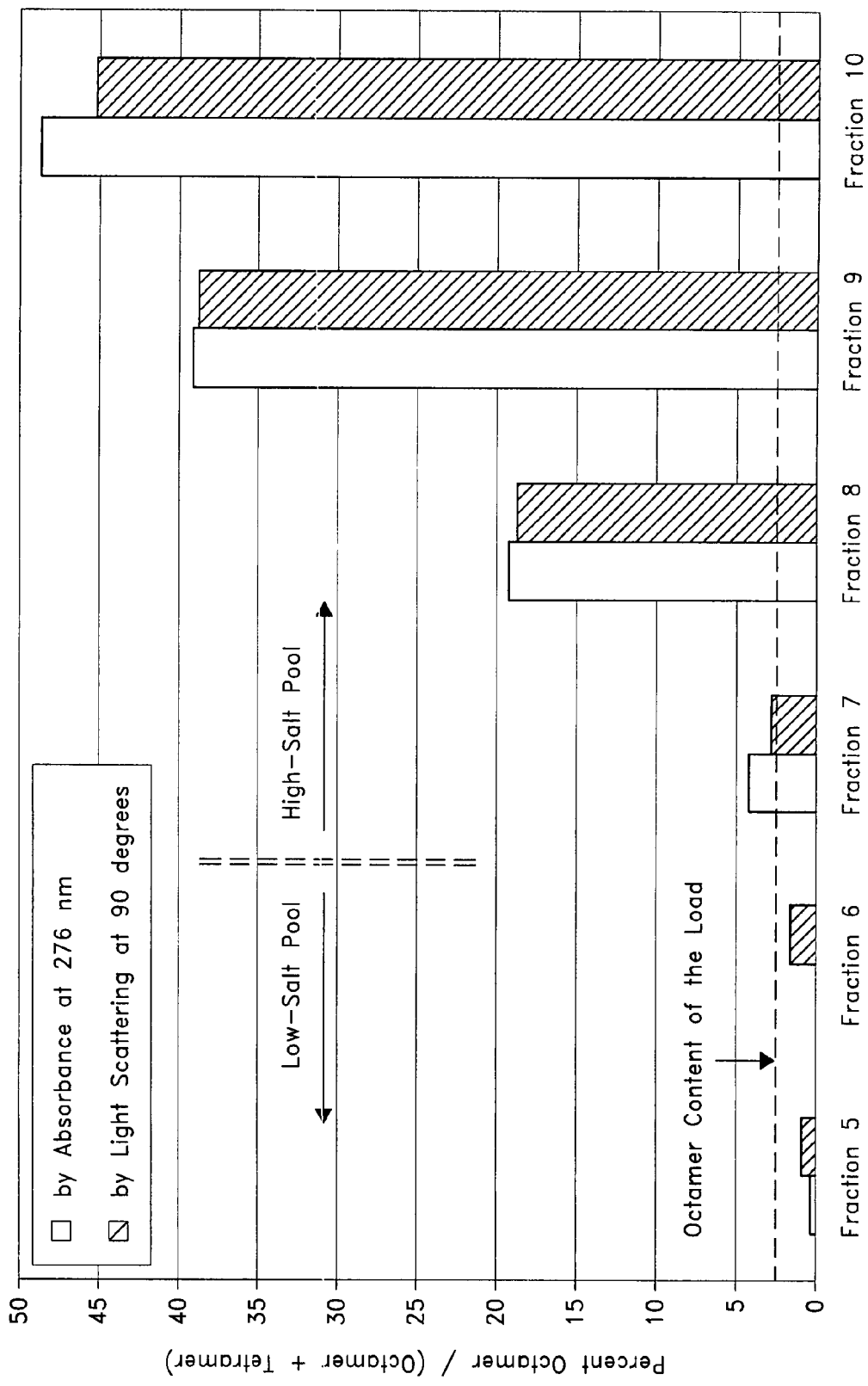
FIG. 4 illustrates octamer content, determined by absorbance at 276 nm and by light scattering at 90°, calculated from the data in FIGS. 2 and 3, of unfractionated PKS uricase and of selected fractions from the preparative MonoQ column chromatography of PKS uricase (FIG. 1).

The results shown in FIGS. 2-4 illustrate the resolution among the tetramer, octamer and larger aggregates of the uricase subunit and the different proportions of the signals detected from these forms of uricase in the various samples. Unlike the absorbance signal, which is directly proportional to the concentration, the light scattering signal is proportional to the product of the concentration times the size of the light scattering unit. The resultant sensitivity of the light scattering detector to very small amounts of highly aggregated uricase revealed the presence of the largest aggregates, which are eluted at or near the void volume (approximately 7 mL).

Example 3

Synthesis of PEG-Uricase Conjugates

Unfractionated PKS uricase (from Bio-Technology General Limited) and the uricase in fractions from the Mono Q column of Example 1 were coupled to 10-kDa PEG using the p-nitrophenyl carbonate derivative of PEG (NPC-PEG) obtained from Shearer ater Polymers (Huntsville, Ala.). The preparation of NPC-PEG from PEG using phenylchloroformates has been described in several reports (e.g. Veronese, F M, et al., (1985) *Appl Biochem Biotechnol* 11:141-152; Kito, M, et al., (1996) *J Clin Biochem Nutr* 21:101-111) and NPC-PEG has been used for the synthesis of PEG-protein conjugates by previous investigator, including the present inventors (e.g. Veronese et al., supra; Sherman, M R, et al., in J M Harris, et al., (Eds.) *Poly(ethylene gleol) Chemistry and Biological Applications. ACS Symposium Series* 680 (pp. 155-176) Washington, D.C.: American Chemical Society). The number of strands of 10-kDa PEG coupled to each subunit of uricase was determined to be six by the method described by Kunitani, M, et al., (1991) *J Chromatogr* 588:125-137.

Example 4

In Vivo Serum Persistence and Immunogenicity of Uricase and PEG-Uricase

PEG conjugates of recombinant mammalian uricases, prepared according to the method of Example 3, were adjusted to 1 mg protein/mL in phosphate-buffered saline (PBS), pH 7.4, for injection. Samples were frozen and stored until analyzed or injected. Samples were warmed to 37° C. for up to 1 hour prior to injection into groups of eight BALB/c female mice. The groups of mice had mean weights in the range of 18-22 g at the start of the studies.

The weights of all mice were monitored and evidence of adverse reactions to the injections or other evidence of ill health was recorded. Twenty-four hours after each of six weekly injections, the animals were anesthetized with ketamine and 100-200 μL of blood was obtained retro-orbitally, except at sacrifice (exsanguination), when a larger volume was collected. Serum was prepared from blood that had clotted for between 4 and 32 hours at 2-8° C. Sera were stored at −20° C. Sera were analyzed for uricolytic activity as described in Example 5 and analyzed for antibodies against uricases as described in Example 6.

Example 5

Uricolytic Activity Assays of PEG-Uricase in Sera from Mice Injected with PEG-Uricase An activity assay based on ultraviolet light absorbance (UV assay) was performed with 100 μM uric acid as the substrate in 200 mM sodium borate, pH 9.2, in a microplate adaptation of the method of I. Fridovich (*J Biol Chem*. (1965) 240:2491-2494). The decrease in absorbance at 292 nm was monitored for 15 minutes at room temperature in a 96-well plate with a UV-transparent bottom (Costar, Corning, N.Y.), using a SpectraMAX 250 microplate reader from Molecular Devices (Sunnyvale, Calif.). The data were analyzed by finding the maximum slope (in milli-absorbance units per minute) of absorbance measurements made during the interval while between 10 and 40% of the substrate was oxidized. Results obtained with this assay are illustrated in FIGS. 1 and 5.

The mean half-life in sera of mice injected for the first time with PKS uricase coupled to six strands of 10-kDa PEG per subunit (6×10-kDa PEG PKS) was 29±14 hours, based on data from sera obtained 24 and 72 hours after the injection.

In separate experiments, it was established that the detectable uricolytic activity in the sera of mice injected with PEG-uricase ceclines during storage at −20° C. and that maximal recovery of this activity is obtained by a 4-hour incubation at 37° prior to assay. FIG. 5 shows that the recovery of uricolytic activity after repeated weekly injections of 6×10-kDa PEG PKS uricase was greatest when the enzyme was purified by Mono Q column chromatography, as in Example 1, prior to PEGylation according to the method of Example 3. Recovery was highest after the injection of conjugates prepared from the high-salt eluate pool of Example 1 (see FIG. 1), which has the smallest content of the very large aggregates (see the light scattering profiles of Fractions 7-10 in FIG. 3). Intermediate recovery was obtained with conjugates prepared from the low-salt eluate pool from the Mono Q column of Example 1, and the poorest recovery was obtained with conjugates made from unfractionated PKS uricase, which has the highest content of very large aggregates (see FIG. 2). The same order of relative activities recovered in sera after repeated injections (high salt pool>low salt pool>unfractionated uricase) was observed regardless of whether the UV assay described above or a calorimetric assay adapted from P. Fossati et al. (*J Clin Chem* (1980) 26:227-231), was used and regardless of whether the sera were incubated at 37° C. before they were assayed.

Example 6

Enzyme-Linked Immunosorbent Assay (ELISA) of Sera from Mice Injected with PEG-Uricase Non-competitive ELISA analyses were performed with porcine uricase bound to 96-well Immulon 2 plates (Dynex Technologies, from VWR Scientific, San Francisco, Calif.). The primary antisera were from mice injected with uricase or 6×10-kDa PEG conjugates prepared according to the method of Example 3. The secondary antibody was goat anti-mouse IgG coupled to horseradish peroxidase (Calbiochem-Novabiochem #401 253, La Jolla, Calif.) and the substrate was o-phenylenediamine dihydrochloride (Sigma P-9187, St. Louis, Mo.), as described by B. Porstmann et al. (*J. Clin. Chem. Clin. Biochem.* (1981) 19:435-440).

FIG. 6 illustrates the results of the non-competitive ELISA analyses. The results demonstrate that the 6×10-kDa PEG PKS uricase synthesized according to the method of Example 3 from the high-salt eluate from the Mono Q column of Example 1 (shown in FIG. 1) did not produce detectable immune responses in any of the eight mice that received weekly injections for six weeks. A few mice injected with conjugates prepared from unfractionated PKS uricase according to the method of Example 3 showed low but detectable immune responses. The highest incidence of immune responses was in mice injected with conjugates prepared according to the method of Example 3 from the low-salt eluate pool from the Mono Q column of Example 1.

Without the benefit of the Light scattering detector for the size-exclusion HPLC analyses, as described in Example 2, it would not have been apparent that the presence of the largest aggregates, not of the octameric form of uricase, is associated with progressively decreased recovery of PEG-uricase conjugates after repeated injections, as observed in Example 5 (FIG. 5) and with an increase in immunogenicity in BALB/c mice, as observed in Example 6 (FIG. 6). These results have important implications for the specifications of the uricase used as a starting material for the production of PEG-uricase for clinical use.

Although the foregoing invention has been described in some detail by way of illustration and example for purposes of clarity of understanding, it is readily apparent to those of ordinary skill in the art in light of the teachings of thus invention that certain changes and modifications may be made thereto without departing from the spirit and scope of that which is described and claimed.

What is claimed is:

1. A purified urate oxidase (uricase) wherein greater than 95% of said uricase is in the tetrameric and octameric forms.

2. The uricase of claim 1, wherein said uricase is a mammalian uricase.

3. The uricase of claim 2, wherein said uricase is porcine liver uricase, bovine liver uricase or ovine liver uricase.

4. The uricase of claim 1, wherein said uricase is recombinant.

5. The uricase of claim 4, wherein said uricase has the amino acid sequence of porcine, bovine, ovine or baboon liver uricase.

6. The uricase of claim 4, wherein said uricase is chimeric.

7. The uricase of claim 6, wherein said chimeric uricase contains portions of porcine liver uricase and portions of baboon liver uricase.

8. The uricase of claim 7, wherein said chimeric uricase is porcine uricase in which arginine residue 291 of SEQ ID NO:1 has been replaced by lysine (R291K) and threonine residue 301 of SEQ ID NO:1 has been replaced by serine (T301S) (PKS uricase).

9. The uricase of claim 4, wherein said uricase has the amino acid sequence as set forth in SEQ ID NO:2, wherein tyrosine residue 97 has been replaced by histidine (Y97H).

10. The uricase of claim 1, wherein said uricase is a fungal or microbial uricase.

11. The uricase of claim 10, wherein said fungal or microbial uricase is isolated from *Aspergillus flavus, Arthrobacter globiformis, Bacillus* sp, or *Candida utilis,* or is a recombinant enzyme having the amino acid sequence of any one thereof.

12. The uricase of claim 1, wherein said uricase is an invertebrate uricase.

13. The uricase of claim 12, wherein said invertebrate uricase is isolated from *Drosophila melanogaster* or *Drosophila pseudoobscura,* or is a recombinant enzyme having the amino acid sequence of any one thereof.

14. The uricase of claim 1, wherein said uricase is a plant uricase.

15. The uricase of claim 14, wherein said plant uricase is isolated from root nodules of *Glycine max* or is a recombinant enzyme having the amino acid sequence thereof.

16. The uricase of claim 1, wherein greater than 97% of said uricase is in the tetrameric and octameric forms.

17. A purified chimeric urate oxidase (uricase), wherein greater than 95% of said uricase is in the tetrameric and octameric forms and wherein said chimeric uricase is porcine uricase in which arginine residue 291 of SEQ ID NO:1 has been replaced by lysine (R291K) and threonine residue 301 of SEQ ID NO:1 has been replaced by serine (T301S) (PKS uricase).

18. A conjugate comprising a purified urate oxidase (uricase) conjugated to poly(ethylene glycol) or poly(ethylene oxide), wherein greater than 95% of said uricase is in the tetrameric and octameric forms.

19. The conjugate of claim 18, wherein greater than 97% of said uricase is in the tetrameric and octameric forms.

20. The conjugate of claim 18, wherein said poly(ethylene glycol) is monomethoxy poly(ethylene glycol).

21. The conjugate of claim 18, wherein said uricase is conjugated to said poly(ethylene glycol) or poly(ethylene oxide) via a linkage selected from the group consisting of urethane (carbamate), secondary amine and amide.

22. The conjugate of claim 18, wherein said poly(ethylene glycol) or poly(ethylene oxide) has an average molecular weight of about 10 kDa to 60 kDa.

23. The conjugate of claim 22, wherein said poly(ethylene glycol) or poly(ethylene oxide) has an average molecular weight of about 10 kDa to 30 kDa.

24. The conjugate of claim 18, wherein the average number of strands of said poly(ethylene glycol) or poly(ethylene oxide) conjugated to said uricase is between about 2 and 12 per uricase subunit.

25. The conjugate of claim 24, wherein said average number of strands of said poly(ethylene glycol) or poly(ethylene oxide) is between about 6 and 10 per uricase subunit.

26. The conjugate of claim 25, wherein said average number of strands of said poly(ethylene glycol) or poly(ethylene oxide) is between about 7 and 9 per uricase subunit.

27. The conjugate of claim 18, wherein said poly(ethylene glycol) or poly(ethylene oxide) is linear.

28. The conjugate of claim 18, wherein said poly(ethylene glycol) or poly(ethylene oxide) is branched.

29. A purified fragment of urate oxidase (uricase), wherein said fragment is a recombinant uricase that has been truncated at the amino terminus, at the carboxyl terminus, or at both the amino and carboxyl termini, and wherein greater than 95% of said truncated uricase is in the tetrameric and octameric forms.

30. The purified uricase fragment of claim 29, wherein greater than 97% of said truncated uricase is in the tetrameric and octameric forms.

31. A conjugate comprising a purified urate oxidase (uricase) conjugated to poly(ethylene glycol) or poly(ethylene oxide), wherein greater than 95% of said uricase is in the tetrameric and octameric forms and wherein the average number of strands of said poly(ethylene glycol) or poly(ethylene oxide) conjugated to said uricase is between about 2 and about 10 per uricase subunit.

32. The conjugate of claim 31, wherein greater than 97% of said uricase is in the tetrameric and octameric forms.

33. The conjugate of claim 31, wherein said poly(ethylene glycol) or poly(ethylene oxide) has an average molecular weight of about 10 kDa to 60 kDa.

34. The uricase conjugate of claim 33, wherein said poly (ethylene glycol) or poly(ethylene oxide) has an average molecular weight of about 10 kDa to 30 kDa.

35. A conjugate comprising a purified urate oxidase (uricase) conjugated to poly(ethylene glycol) or poly(ethylene oxide), wherein greater than 95% of said uricase is in the tetrameric and octameric forms, wherein the average number of strands of said poly(ethylene glycol) or poly(ethylene oxide) conjugated to said uricase is between about 2 and 10 per uricase subunit and wherein said poly(ethylene glycol) or poly(ethylene oxide) has an average molecular weight of about 10 kDa to 60 kDa.

36. The uricase conjugate of claim 35, wherein greater than 97% of said uricase is in the tetrameric and octameric forms.

37. A pharmaceutical composition for lowering uric acid levels in a body fluid or tissue, comprising a purified urate oxidase (uricase) conjugated to poly(ethylene glycol) or poly (ethylene oxide) and a pharmaceutically acceptable carrier, wherein greater than 95% of said uricase is in the tetrameric and octameric forms.

38. The pharmaceutical composition of claim 37, wherein said composition is stabilized by lyophilization and dissolves upon reconstitution to provide a solution suitable for parenteral administration.

39. An isolated urate oxidase (uricase) prepared by a method comprising separating uricase aggregates larger than octamers from uricase tetramers and octamers and excluding such aggregates from the isolated uricase, wherein greater than 95% of said isolated uricase is in the tetrameric and octameric forms.

40. The uricase of claim 39, wherein greater than 97% of said isolated uricase is in the tetrameric and octameric forms.

* * * * *

UNITED STATES PATENT AND TRADEMARK OFFICE
CERTIFICATE OF CORRECTION

PATENT NO.       : 7,927,852 B2
APPLICATION NO.  : 11/882750
DATED            : April 19, 2011
INVENTOR(S)      : Sherman et al.

It is certified that error appears in the above-identified patent and that said Letters Patent is hereby corrected as shown below:

Title Page
Item (73), Assignee Section, please add --Duke University, Durham, NC (US)-- to "Mountain View Pharmaceuticals, Inc., Menlo Park, CA (US)".

Signed and Sealed this
Fifth Day of July, 2016

Michelle K. Lee
*Director of the United States Patent and Trademark Office*